US008712151B2

(12) United States Patent
Zhao et al.

(10) Patent No.: US 8,712,151 B2
(45) Date of Patent: Apr. 29, 2014

(54) METHOD AND STRUCTURE FOR IMAGE LOCAL CONTRAST ENHANCEMENT

(75) Inventors: Wenyi Zhao, Mountain View, CA (US); Simon P. DiMaio, Sunnyvale, CA (US); Catherine J. Mohr, Mountain View, CA (US); David D. Scott, Oakland, CA (US); Tao Zhao, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 430 days.

(21) Appl. No.: 13/026,740

(22) Filed: Feb. 14, 2011

(65) Prior Publication Data

US 2012/0209287 A1 Aug. 16, 2012

(51) Int. Cl.
*G06K 9/00* (2006.01)
(52) U.S. Cl.
USPC .......................................... 382/167; 382/169
(58) Field of Classification Search
None
See application file for complete search history.

(56) References Cited

U.S. PATENT DOCUMENTS

| 8,103,120 | B2 * | 1/2012 | Choi et al. | 382/274 |
|---|---|---|---|---|
| 2003/0012434 | A1 * | 1/2003 | Kanai | 382/167 |
| 2003/0161549 | A1 * | 8/2003 | Lei et al. | 382/274 |
| 2005/0052544 | A1 * | 3/2005 | Tsai | 348/223.1 |
| 2008/0056566 | A1 * | 3/2008 | Shehata et al. | 382/167 |
| 2009/0169129 | A1 * | 7/2009 | Li et al. | 382/274 |
| 2009/0214111 | A1 * | 8/2009 | Zinaty et al. | 382/167 |
| 2010/0157112 | A1 * | 6/2010 | Miyagi | 348/242 |
| 2011/0116713 | A1 * | 5/2011 | Zeng et al. | 382/167 |
| 2011/0134328 | A1 * | 6/2011 | Tomioka et al. | 348/652 |

FOREIGN PATENT DOCUMENTS

WO WO2010042522 A1 4/2010

OTHER PUBLICATIONS

Guichard, Frederic et al., "Extended depth-of-field using sharpness transport across color channels," Proceedings of Electronic Imaging, 2009, SPIE, 13 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Burt, Peter J. and Edward J. Adelson, "The Laplacian Pyramid as a Compact Image Code," IEEE Transaction on Communications, vol. Com-31, No. 4, Apr. 1983, pp. 532-540.
"Color Filter Array Designs," No date, 22 pages, http://www.quadibloc.com/other/cfaint.htm Last visited Dec. 13, 2010.

(Continued)

*Primary Examiner* — Jingge Wu

(57) ABSTRACT

A local contrast enhancement method transforms a first plurality of color components of a first visual color image into a modified brightness component by using a first transformation. The first plurality of color components are in a first color space. The modified brightness component is a brightness component of a second color space. The second color space also includes a plurality of chromatic components. The method transforms all the color components of the first color space into the chromatic components of the second color space. The method then transforms the modified brightness component and the chromatic components of the second color space into a plurality of new color components, in the first color space, of a second visual color image. The method transmits the plurality of new color components to a device such as a display device. The second visual color image has enhanced contrast in comparison to the first visual color image.

21 Claims, 12 Drawing Sheets
(2 of 12 Drawing Sheet(s) Filed in Color)

(56) References Cited

OTHER PUBLICATIONS

Discovery Scientific, "YUV, YCbCr, YPbPr color spaces," 2010, 2 pages, http://discoverybiz.net/enu0/faq/faq_YUV_YCbCr_YPbPr.html Last visited Dec. 15, 2010.

Gimel'Farb, Georgy, "CBIR: Color Features," Lecture Notes, 2006, 17 pages, http://www.cs.auckland.ac.nz/compsci708s1c/lectures/Glect-html/topic3c708FSC.htm Last visited Dec. 15, 2010.

Gimel'Farb, Georgy, "Part 2. Content-Based Video Information Search and Retrieval," Lecture Notes, 2006, 2 pages http://www.cs.auckland.ac.nz/compsci708s1c/lectures/Glect-html/top708-2006.html Last visited Dec. 15, 2010.

Gono, K., "Multifunctional Endoscopic Imaging System for Support of Early Cancer Diagnosis," IEEE Journal of Selected Topics in Quantum Electronics, vol. 14, No. 1, Jan./Feb. 2008, pp. 62-69, IEEE.

Intel, Product Documentation, "Color Models," No date, 13 pages, http://software.intel.com/sites/products/documentation/hpc/ipp/ippi/ippi_ch6/ch6_color_models.html Last visited Dec. 15, 2010.

Intel, Product Documentation, "Image Color conversion," No Date, 9 pages, http://software.intel.com/sites/products/documentation/hpc/ipp/ippi/ippi_ch6/ch6_Intro.html Last visited Dec. 15, 2010.

Jain, Anil K., "Fundamentals of Digital Image Processing," Prentice Hall, 1989, Section 7.3, pp. 241-244.

Muto, Manabu et al., "Narrow-band imaging of the gastrointestinal tract," Journal of Gastroenterology, 2009, vol. 44, pp. 13-25, Springer.

\* cited by examiner

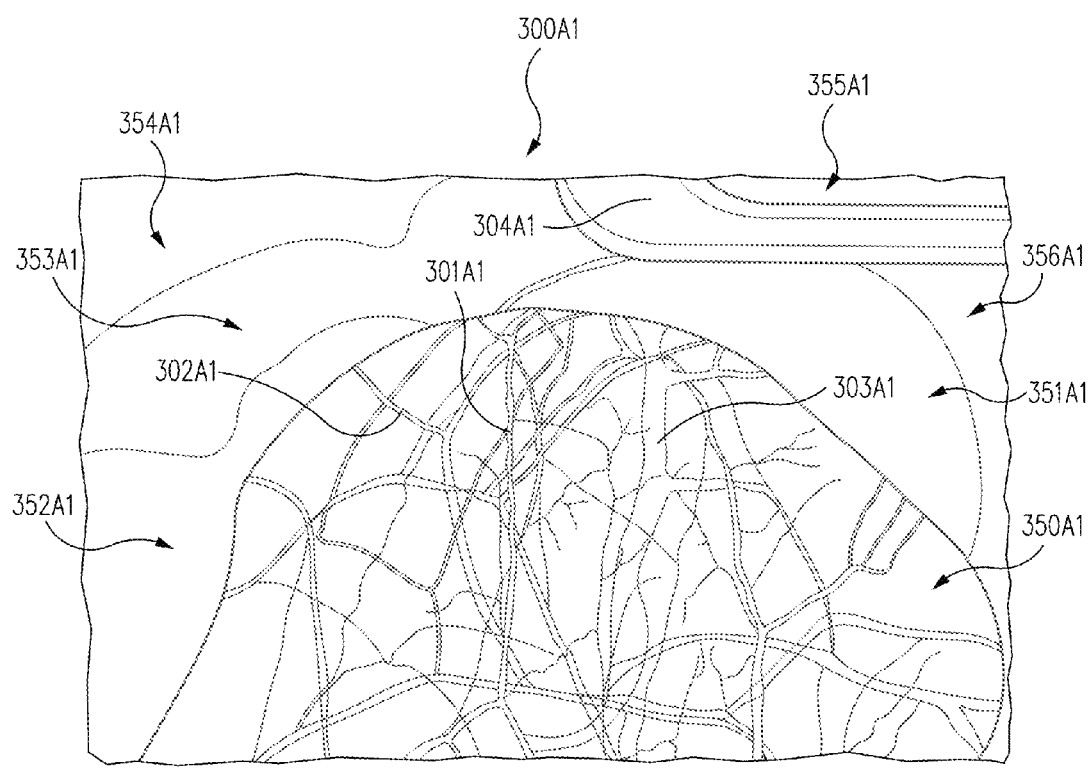
FIG. 3A1

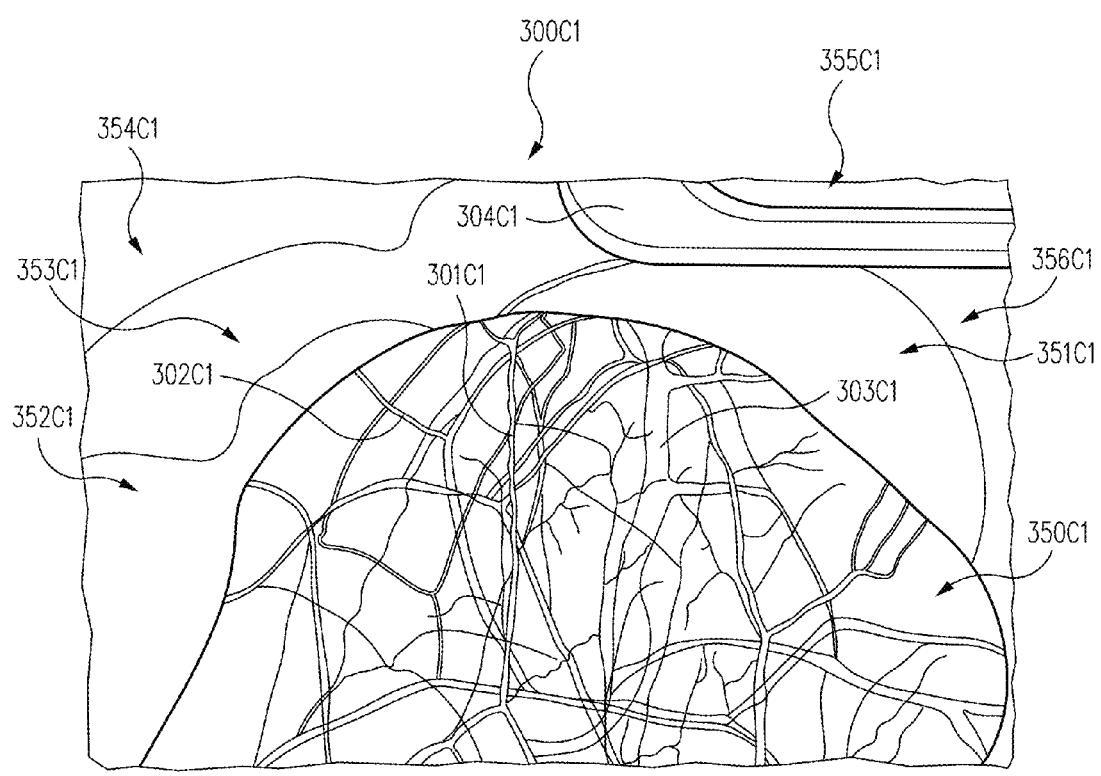
FIG. 3C1

METHOD AND STRUCTURE FOR IMAGE LOCAL CONTRAST ENHANCEMENT

BACKGROUND

1. Field of Invention

Aspects of this invention are related to color imaging, and are more particularly related to enhancing contrast in a color image.

2. Related Art

The da Vinci® Surgical System, commercialized by Intuitive Surgical, Inc., Sunnyvale, Calif., is a minimally invasive teleoperated surgical system that offers patients many benefits, such as reduced trauma to the body, faster recovery, and shorter hospital stay. One key component of the da Vinci® Surgical System is a capability to provide two-channel (i.e., left and right) video capture and display of visible images to provide stereoscopic viewing for the surgeon.

Such electronic stereoscopic imaging systems may output high definition video images to the surgeon. These systems also may allow features such as zoom to provide a "magnified" view that allows the surgeon to identify specific tissue types and characteristics, as well as to work with increased precision. In a typical surgical field image, however, certain tissue types are difficult to identify, or tissue of interest may be at least partially obscured by other tissue. Hence, various augmented modes of viewing have been developed in addition to the normal display mode. The surgeon typically switches back and forth between an augmented viewing mode and a normal display mode to see selected tissue with increased precision.

The augmented viewing modes are intended to assist the surgeon in differentiating structures in the image. One prior art augmented viewing mode uses a narrow band imaging system. This system utilizes narrow band spectrum illumination to highlight structures that are not easily seen under normal wide band visual spectrum illumination. The display for the narrow band images is typically pseudo colored by converting green and blue color components to three component colors. As a result, the surgeon needs to switch back and forth between the normal red-green-blue viewing mode and the narrow band viewing mode. See for example, M. Muto et al., "Narrow-band imaging of the gastrointestinal tract," *J. Gastenterology*, Vol. 44 pp. 13-25 (2009). See also, K. Gono, "Multifunctional Endoscopic Imaging System for Support of Early Cancer Diagnosis," *IEEE Journal of Selected Topics in Quantum Electronics*, Vol. 14, pp. 62-69 (2008).

SUMMARY

Human perception of a color image is sensitive to the local brightness change, i.e., local contrast, of a color image. Thus, the methods described herein are designed to increase the local contrast while preserving the apparent global brightness to the extent possible, via discarding some or all of one color component of an original color image when determining a new brightness of pixels in a new contrast enhanced color image.

In one aspect, the methods are based on physical properties of imaging and human perception of surgical content to digitally enhance local contrast for surgical images. The contrast enhanced color images allow surgeons to more easily differentiate critical structures, such as blood vessels, from surrounding tissues.

In surgical imaging, the predominant color is red for both tissues and blood vessels, making it difficult for surgeons to differentiate critical structures from surrounding tissues. In addition, the red color component has lower contrast compared to the green and blue color components. This lower contrast characteristic makes it even harder to differentiate fine structures from surrounding tissues. The contrast enhancement methods, in one aspect, improve the image contrast by removing, or at least reducing, the contrast contribution from the red component while keeping the true color of the color images unchanged.

A local contrast enhancement method transforms a first plurality of color components of a first visual color image into a modified brightness component using a first transformation. The first plurality of color components are color components in a first color space. The modified brightness component is a brightness component of a second color space. The second color space includes a plurality of chromatic components in addition to the brightness component. The transformation is different from a standards transformation that transforms all color components of the first color space into a brightness component of the second color space.

The local contrast enhancement method also transforms all the color components of the first color space into the chromatic components of the second color space. The method then transforms the modified brightness component and the chromatic components of the second color space into a plurality of new color components, in the first color space, of a second visual color image. The plurality of new color components includes all the color components in the first color space. In one aspect, these three transformation processes are performed in a single transformation process. Following the last transformation, the method transmits the plurality of new color components to a device such as a display device. The second visual color image has enhanced contrast in comparison to the first visual color image.

In one aspect, the first visual color image is received from an endoscopic camera so that the first visual color image is a color image of a surgical site. The method also includes capturing light from a stereoscopic endoscope by the endoscopic camera. The captured light comprises the first visual color image.

In another aspect, the first color space in the local contrast enhancement method has red, green, and blue color components, and the second color space has a luminance component and two chromatic components. Here, the first plurality of color components is the blue color component and the green color component, and the modified brightness component in the second color space is a modified luminance component.

In one aspect, transforming the first plurality of color components of the first visual color image includes performing a scaling process. The scaling process is performed on less than all the color components in the first color space so that a first plurality of color components includes less than all the color components in the first color space. In one aspect, the first plurality of color components includes a green color component. In another aspect, performing the scaling process includes using a same scaling factor for the first plurality of color component for all pixels in the first visual color image. In still yet another aspect, performing the scaling process includes using an adaptive scaling factor where a different scaling factor is used for different sets of pixels in the color image.

In a further aspect of the local enhanced contrast method, transforming the first plurality of color components of the first visual color image includes performing a brightness compensation process so that the modified brightness component includes brightness compensation. In one aspect, the brightness compensation process includes biasing a coefficient in the standards transformation for one of the color components in the first plurality prior to transforming the first plurality. Here, the first plurality includes all the color components in the first color space. Following the biasing, all the color components in the first color space are transformed to an intermediate brightness component in the second color space by using a transformation including the biased coefficient. In this aspect, transforming the first plurality further includes scaling the intermediate brightness component to generate the modified brightness component with compensation.

In another aspect, transforming a first plurality of color components includes transforming less than all the color components in the first color space into a first intermediate brightness component in the second color space. In this aspect, the brightness compensation process includes adding a constant to the first intermediate brightness component to obtain a second intermediate brightness component. Transforming the first plurality of color components further includes scaling the second intermediate brightness component to generate the modified brightness component with brightness compensation.

In still yet another aspect, transforming the first plurality of color components includes generating a plurality of pyramids having a plurality of levels, wherein each level has a different image resolution. In still yet a further aspect, transforming the first plurality of color components includes performing a histogram matching process. The histogram matching process maintains the global brightness of the first visual color image in the second visual color image.

A minimally invasive surgical system includes a camera and a control system coupled to the camera. The camera captures light and creates a first visual color image having a first plurality of color components in a first color space. The control system includes a contrast improvement module. The contrast improvement module transforms the first visual color image to a second visual color image with enhanced contrast relative to the first visual color image by mapping the first plurality of color components into a modified brightness component and chromatic components of a second color space, and then mapping the modified brightness component and chromatic components to a new plurality of color components, in the first color space, of a second visual color image.

The system also includes a display device coupled to the contrast improvement module to receive the second visual color image. The display device displays the second visual color image with the enhanced contrast relative to the first visual color image.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3A1 is a black and white line representation of the color image of FIG. 3A.

FIG. 3C1 is a black and white line representation of the color image of FIG. 3C.

Figure 1:
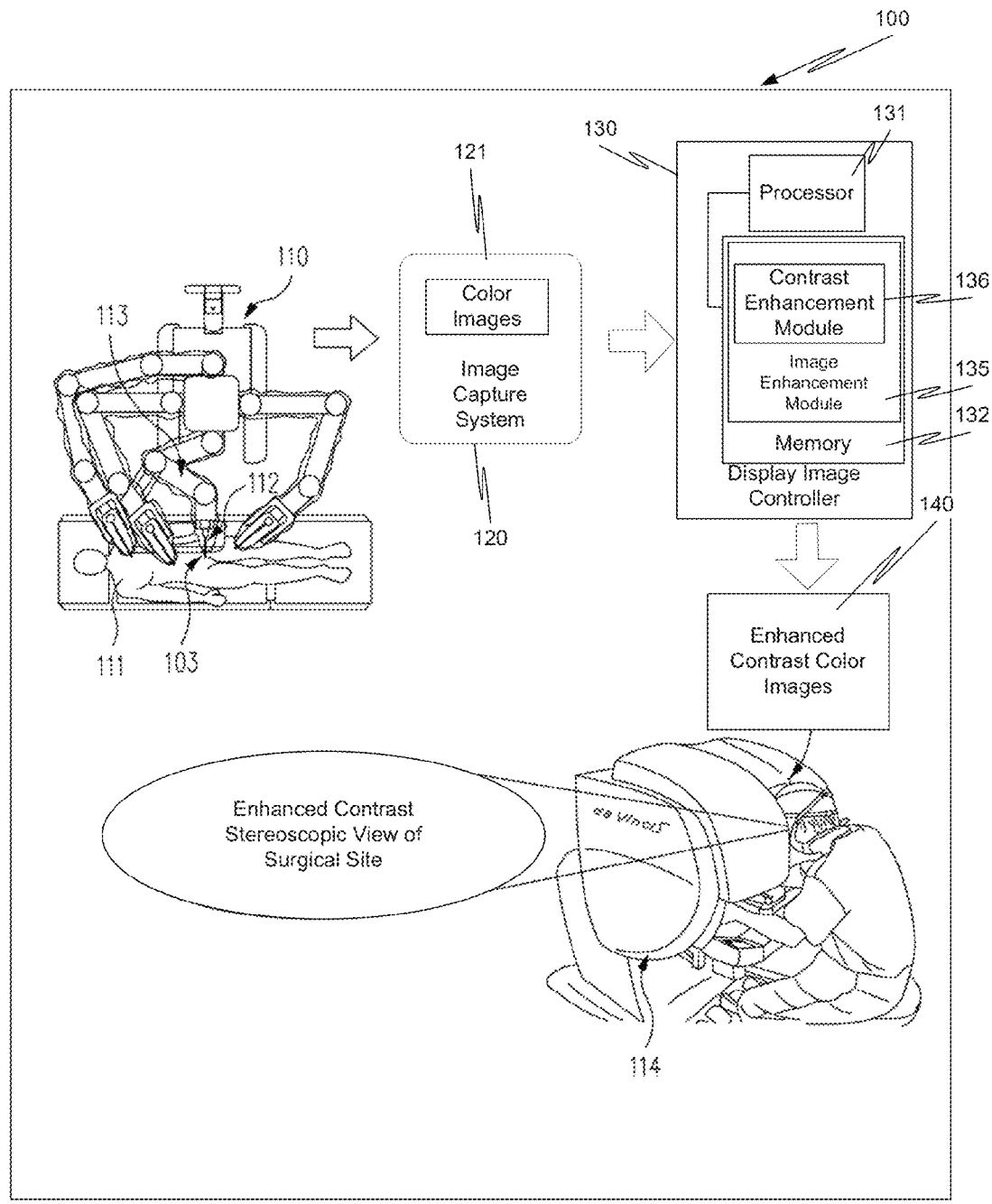
FIG. 1 is a high level diagrammatic view of a minimally invasive teleoperated surgical system that includes a contrast enhancement module.

In the drawings, the first digit of a reference number indicates the figure in which the element with that reference number first appears.

DETAILED DESCRIPTION

Aspects of this invention augment the stereoscopic viewing capability of a minimally invasive surgical system, e.g., the da Vinci® minimally invasive teleoperated surgical system commercialized by Intuitive Surgical, Inc. of Sunnyvale, Calif., by enhancing the contrast of color images. (DA VINCI® is a registered trademark of Intuitive Surgical, Inc. of Sunnyvale, Calif.) Enhanced contrast color images 140 provide an enhanced contrast stereoscopic image of a surgical site for the surgeon.

The enhanced contrast stereoscopic image provides the surgeon with a better perceived depth of field, e.g., the blood vessels appear to stand out more, and an enhanced effective perceived sharpness. The enhanced contrast combined with the perceived enhancement of the depth of field and effective sharpness reduces surgeon fatigue associated with viewing the surgical site. With the enhanced contrast, structures in the image appear to stand out more clearly without requiring switching back and forth between different viewing modalities as in the prior art.

The enhanced contrast stereoscopic image is provided in real time to a surgeon performing a surgical procedure by using minimally invasive teleoperated surgical system 100. As explained more completely below, enhanced contrast color images 140 are formed using a transformation that converts color components in color images 121 to new color components for the color images with enhanced contrast.

This enhanced local contrast process is done by modifying a brightness component of the original color image while maintaining the color information in the enhanced contrast color images. Thus, compared with the original color image, not only is the contrast of the color image increased, but also there is no loss in detail. Rather, as explained above, the stereoscopic enhanced contrast visible color images are superior to the normal stereoscopic visible color images.

Prior to considering the enhanced contrast process in further detail, several concepts and definitions used in the enhanced contrast process are considered.

Digitized color images include a plurality of pixels. For example, a color image that is 1920 by 1080 has 1080 rows of pixels and each row includes 1920 pixels. Each pixel typically has three color components that when combined determine the color of that pixel.

The color components are defined by a color space. Typical color spaces include: a color space that includes a red color component R, a green color component G, and a blue color component B; a YUV color space that includes a luminance component Y and two chromatic components U and V; a YCbCr color space that includes a luminance component Y and two chromatic components Cb and Cr; and a color space that includes a hue component, a saturation component, and a brightness component. This list of color spaces and of the components included in the color spaces is illustrative only and is not intended to be limiting to these specific color spaces. Aspects of the invention may be applied in various color spaces Herein, a color space that includes a red color component R, a green color component G, and a blue color component B is referred to as a RGB color space. Each color component in the RGB color space is measured, in one aspect, with a value ranging from zero to 255, where zero is no light and 255 is maximum intensity.

The range of values used herein is for illustration only and are not intended to be limiting. As is known to those knowledgeable in the field, a color component with a value ranging from zero to 255 is stored as one byte of data. If more bytes of data are used for a color component, the number of possible values changes.

The luminance components in the YUV and YCbCr color spaces and the brightness component in the hue, saturation, and brightness color space represent the apparent brightness of a pixel. The apparent brightness is defined by a grayscale. The grayscale has a range from black to white with varying shades of grey between black and white. The values of the grayscale, in one aspect, range from 0 to 255, where a value of zero represents black and a value of 255 represents white. Values between zero and 255 represent various shades of gray.

Herein, a brightness component refers to a component in a color space that is an apparent brightness and that is a grayscale component. The brightness component is not a color component because the brightness component conveys only brightness information and not color information. In color spaces with a brightness component, the color components are the components of the color space other than the brightness component and are referred to herein as chromatic components.

Human perception of a color image is sensitive to the local brightness change, i.e., local contrast, of a color image. Thus, the following methods are designed to increase the local contrast while preserving the apparent global brightness to the extent possible, via discarding some or all of one color component of an original color image when determining a new brightness of pixels in a new contrast enhanced color image.

Methods, which are described more completely below, digitally enhance local contrast for surgical images based on physical properties of imaging and human perception of surgical image content. The contrast enhanced color images allow surgeons to more easily differentiate critical structures such as blood vessels from surrounding tissues.

In surgical imaging, the predominant color is red for both tissues and blood vessels, making it difficult for surgeons to differentiate critical structures from surrounding tissues. In addition, as explained more completely below, the red color component appears to be fuzzy compared to the green and blue color components, apparently due to relatively deeper tissue penetration of complex biological structures by the red color component. This is especially true in close-range imaging. This makes it even more difficult to differentiate fine structures from surrounding tissues. The methods described below enhance the color image contrast by removing, or at least reducing, the contrast contribution from the red component while keeping the true color of the color images unchanged.

In the following examples, color images of surgical sites are considered. However, the use of surgical images is illustrative only and is not intended to be limiting. The methods described below for enhancement of contrast are also applicable to a system in which the response for one of a plurality of components in a color space is degraded. The degradation could be the result of poor optical system response, poor calibration of electronic components, failure of electronic components, etc. In each instance, the component in the color space associated with the degradation is not used in determining the brightness that provides enhanced contrast.

FIG. 1 is a high level diagrammatic view of a minimally-invasive teleoperated surgical system 100, for example, the da Vinci® Surgical System. System 100 includes a display image controller 130 that includes a contrast enhancement module 136, which in this example is included within an image enhancement module 135. Contrast enhancement module 136 is stored in a memory 132 and executed on a processor 131 to perform method 200 (FIG. 2), which is described more completely below. This is illustrative only and is not intended to be limiting. Module 136 may be processed by a microprocessor, field programmable gate array (FPGA), or other controller, and may include operations performed by hardware, firmware, or software, other circuitry, or any combination thereof.

Also, contrast enhancement module 136 is shown as the only module in image enhancement module 135 in memory 132. Image enhancement module 135 can also include other modules used to enhance the color image displayed on surgeon's console 114. For example, image enhancement module 135 may include a sharpness enhancement module, such as the widely used unsharp mask.

In this example, a surgeon, using a surgeon's console 114, remotely manipulates an endoscope 112 mounted on a robotic manipulator arm 113. There are other parts, cables, etc. associated with the da Vinci® Surgical System, but these are not illustrated in FIG. 1 to avoid detracting from the disclosure. Further information regarding minimally invasive surgical systems may be found for example in U.S. patent application Ser. No. 11/762,165 (filed Jun. 13, 2007; disclosing Minimally Invasive Surgical System; published as U.S. Patent Application Publication No. US 2008/0065101 A1) and U.S. Pat. No. 6,331,181 (filed Dec. 18, 2001; disclosing Surgical Robotic Tools, Data Architecture, and Use), both of which are incorporated herein by reference.

An illumination system (not shown) is coupled by a fiber optic bundle to endoscope 112. The illumination system provides at least white light illumination that includes a plurality of visible color illumination components. The light passes through at least one illumination path in endoscope 112 and illuminates tissue 103 of a patient 111.

Endoscope 112 also includes, in one aspect, two optical channels, e.g., a left channel and a right channel, for passing light reflected from the tissue, e.g., reflected white light. The reflected white light is used to form a visible color image or images. Specifically, the white light reflected from tissue 103 is captured as left and right visible color images 121 in image capture system 120. Each color image may be captured by a single sensor device or by two or more sensor devices.

Figure 2:
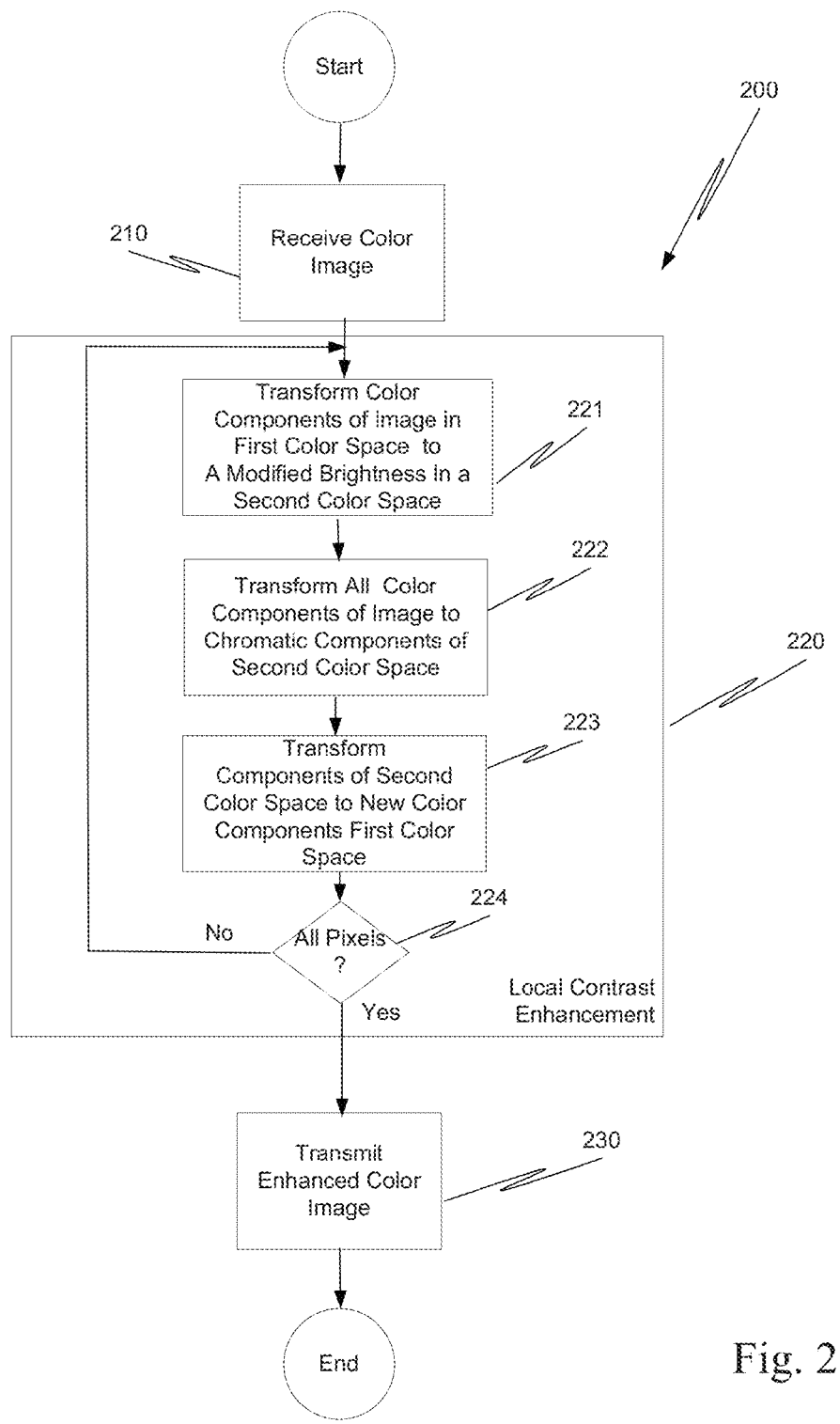
FIG. 2 is a process flow diagram of a local contrast enhancement process.

Display image controller 130 receives the color components of the acquired visible color images from image capture system 120 in RECEIVE COLOR IMAGE process 210 of method 200 (FIG. 2). LOCAL CONTRAST ENHANCEMENT process 220 receives the color components that make up the received color image.

In the following examples, the color components processed in LOCAL CONTRAST ENHANCEMENT process 220 are red, green, and blue color components R, G, B. LOCAL CONTRAST ENHANCEMENT process 220 transforms a first set of RGB color components (R, G, B) of the received color image into a second set of RGB color components (Knew, Gnew, Bnew) of a color image with enhanced contrast in comparison to the color image that was received in RECEIVE COLOR IMAGE process 210. This can be expressed as:

$$\begin{pmatrix} Rnew \\ Gnew \\ Bnew \end{pmatrix} = A \begin{pmatrix} R \\ G \\ B \end{pmatrix}$$

where A is a transformation process performed by LOCAL CONTRAST ENHANCEMENT process 220 to enhance the contrast of the received color image.

As is known to those knowledgeable in the field, transformation process A includes a plurality of transformations. Each transformation in turn includes, for example, a transform that is followed by a shift process. When transformation process A includes both a transform and the inverse of that transform, the shift processes cancel out. If transformation process A does not include both a transform and the inverse of that transform, the appropriate shift is applied after all the transforms in transformation process A are completed. One knowledgeable in the field understands how to choose a consistent standard such that the shift processes cancel out and any normalization can be applied to coefficients used in the transformation. For example, the MATLAB product that is available from The Mathworks, Inc. of Natick, Mass., U.S. includes color space transformations that are consistent with respect to shifting for the various color space transformations discussed herein. Accordingly, the shift processes are not considered in further detail herein to avoid detracting from the disclosure.

Several examples of LOCAL CONTRAST ENHANCEMENT process 220 are described more completely below. The examples are illustrative only and are not intended to be limiting. Also, a single color image of surgical site is used in the examples. If a monoscopic endoscope is used, only a single color image is processed using method 200. If a stereoscopic endoscope is used, the left and right color images are individually processed using method 200.

Figure 3A:
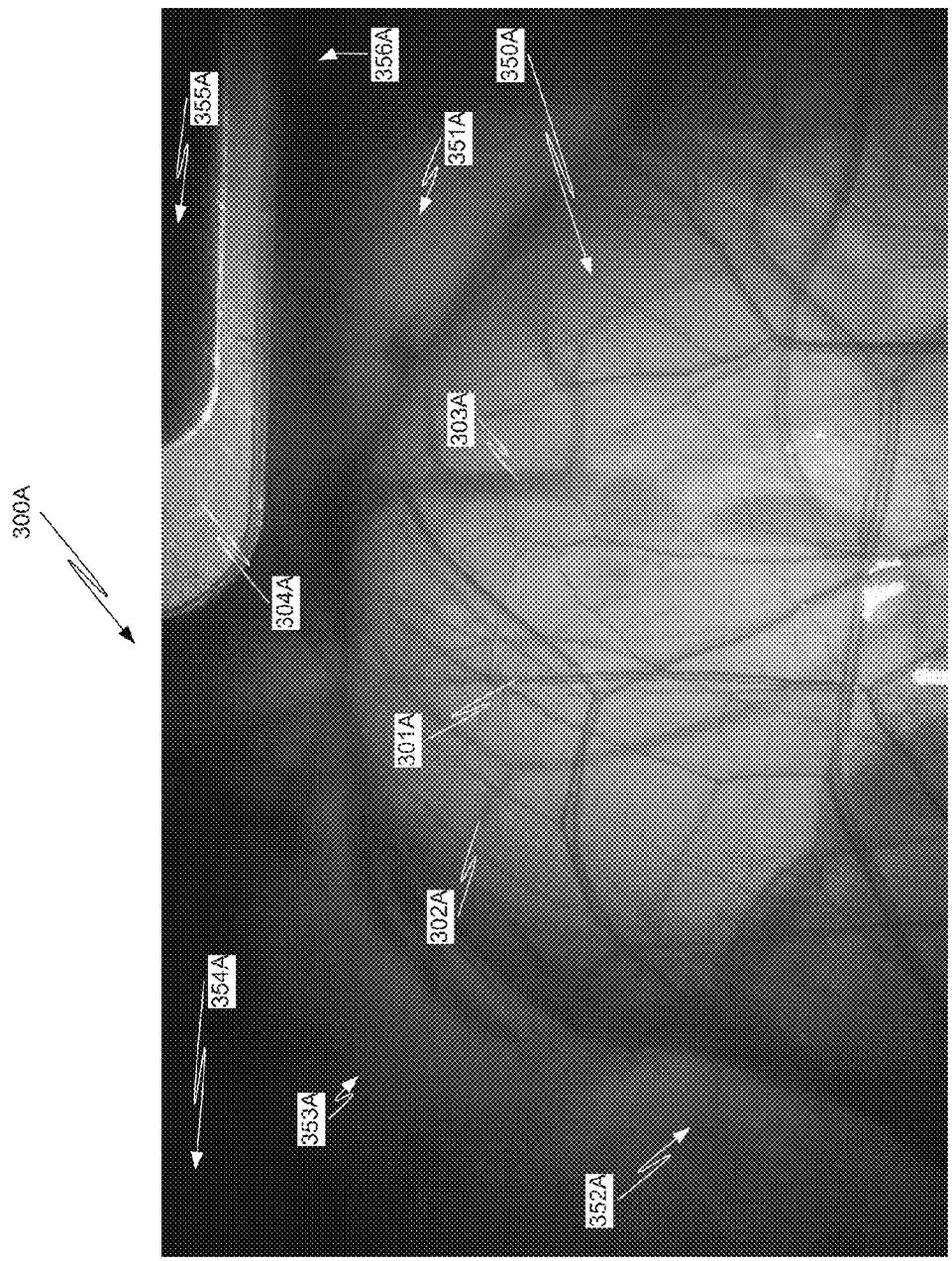
FIG. 3A is an example of a color image that is received in the local contrast enhancement process of FIG. 2.

FIG. 3A is one example of a color image 300A that is received in RECEIVE COLOR IMAGE process 210. The color image has a general fuzzy appearance so that blood vessels 301A, 302A, and 303A, for example, are visible but do not stand out clearly from the other parts of the color image. In a stereoscopic system, where both the left and right color images have this fuzziness, the surgeon perceives a poor quality stereoscopic image.

Typically, in surgical color images, the red color component is the dominant component. However, the red color component provides little spatial information. For example, consider two representative pixels 310, 311 (FIG. 3B) in color image 300.

Figure 3B:
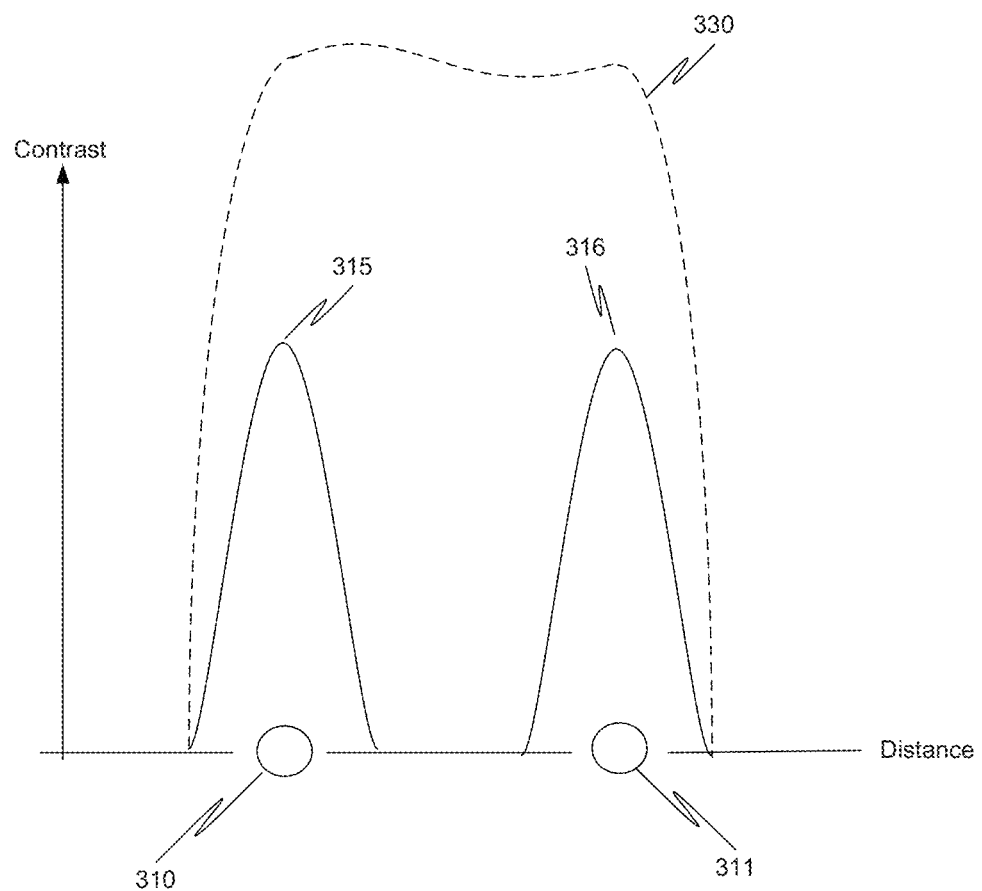
FIG. 3B is a graph that illustrates the contrast for three color components for two pixels in a color image.

In FIG. 3B, curve 330 represents the contrast for the red color component of pixels 310, 311. For simplicity, the blue and green color components are assumed to have identical contrast. Thus, curve 315 represents the contrast of the blue and green color components for pixel 310, while curve 316 represents the contrast of the blue and green color components for pixel 311.

Notice that red color component contrast curve 330 provides little or no spatial information between pixels 310, 311. However, blue and green color component contrast curves 315, 316 provide clear spatial separation between pixels 310 and 311. This example demonstrates that the predominance of the red color component and that the nature of the red color component contrast curve contributes to the fuzziness of color image 300A.

As explained more completely below, local contrast enhancement process 220 enhances the contrast of each pixel in a color image, i.e., enhances the local contrast, by effectively removing or reducing the red color component contribution to the contrast when determining the brightness of a pixel. In one example, the red color component is removed in the brightness determination, and the brightness is determined based on the blue and green color components. Color image 300C (FIG. 3C) was generated using method 200 with color image 300A as the input color image. Notice that in color image 300C the perceived fuzziness of color image 300A is gone, and that no artifacts have been introduced by enhancing the contrast.

Notice also, for example, that blood vessels 301C, 302C, 302C appear to stand out more relative to the background tissue due to the enhanced contrast. Consequently, in the enhanced color image stereoscopic view, the surgeon has a better perceived depth of field. The enhanced contrast also is perceived by the surgeon as enhancement of effective sharpness of the stereoscopic image. Thus, the enhanced contrast provides a better stereoscopic image that clearly separates structures in the image, and so it reduces surgeon fatigue associated with viewing the surgical site.

Figure 3C:
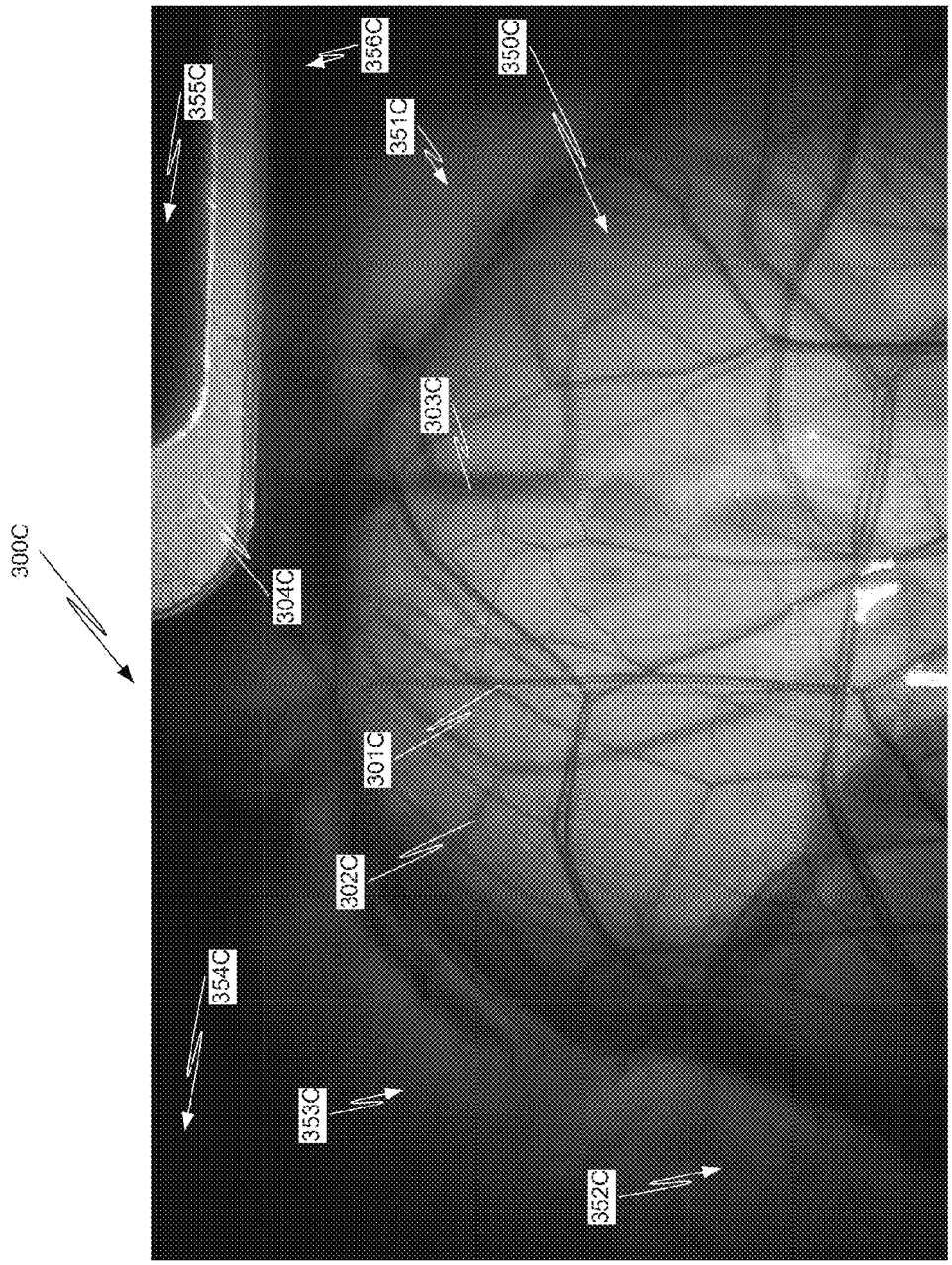
FIG. 3C is an example of a color image that is output from the local contrast enhancement process of FIG. 2.

FIG. 3A1 is a black and white line drawing 300A1 of input color image 300A (FIG. 3A), and FIG. 3C1 is a black and white line drawing 300C1 of contrast enhanced color image 300C (FIG. 3C). Region 350A in color image 300A, which corresponds to region 350A1 (FIG. 3A1), is the brightest region in color image 300A, and generally has a pinkish red color. The blood vessels are red. The gray lines in region 350A1 of FIG. 3A1 represent the fuzzy red blood vessels in the color image.

Regions 351A, 352A, and 353A in color image 300A, which correspond to regions 351A1, 352A1, and 353A1, respectively, in image 300A1, are darker than region 350A, but these regions still have a generally pinkish red color. The blood vessels are red and are less distinct than the blood vessels in brightest region 350A of FIG. 3A. Thus, in FIG. 3A1, no blood vessels are shown in regions 351A1, 352A1, and 353A1.

Regions 354A, 355A and 356A in color image 300A, which correspond to regions 354A1, 355A1, and 356A1, respectively, in FIG. 3A1, are very dark and nearly black. Surgical instrument 304A in color image 300A corresponding to surgical instrument 300A1 in FIG. 3A1 is silver in color.

In FIG. 3C1, region 350C1 corresponds to region 350C in FIG. 3C. Region 350C is the brightest region in color image 300C. Region 350C has a pinkish red color and the blood vessels are red with enhanced contrast. The black lines in region 350C1 of FIG. 3C1 represent the contrast enhanced red blood vessels in the color image.

Regions 351C, 352C, and 353C in color image 300C, which correspond to regions 351C1, 352C1, and 353C1, respectively, in image 300C1, are darker than region 350C, but these regions still have a pinkish red color. The blood vessels are red and less distinct than the blood vessels in brightest region 350C of FIG. 3C. Thus, in FIG. 3C1, no blood vessels are shown in regions 351C1, 352C1, and 353C1.

Regions 354C, 355C and 356C in color image 300C, which correspond to regions 354C1, 355C1, and 356C1, respectively, in FIG. 3C1, are very dark and nearly black. Surgical instrument 304C in color image 300C corresponding to surgical instrument 300C1 in FIG. 3C1 is silver in color.

Images 300A, 300A1, 300C, and 300C1 are illustrative only and are not intended to be limiting. The method and structures described herein can be used on a wide variety of color images including images other than surgical images.

Returning to FIG. 2, TRANSFORM COLOR COMPONENTS OF IMAGE IN FIRST COLOR SPACE TO A MODIFIED BRIGHTNESS IN A SECOND COLOR SPACE process 221 enhances the brightness, e.g., the local contrast of pixels, of the color image received in RECEIVE COLOR IMAGE process 210. In the following examples, the first color space in process 221 is the RGB color space, and the second color space is the YCbCr color space. The use of these color spaces is illustrative only and is not intended to be limiting to these specific color spaces. In view of this disclosure, LOCAL CONTRAST ENHANCEMENT process 220 can be implemented for various color spaces appropriate for a particular application of method 200.

Also, for medical color images of surgical sites, as described above, red color component R does not provide any useful contrast information. Thus, in one aspect, process 221 transforms the blue color component B and green color component G to generate an intermediate brightness component, which in this example is luminance component Ygb. The intermediate brightness component is further processed to generate a modified brightness component in the second color space, e.g., to generate modified luminance component Ynew in second color space YCbCr. This processing compensates for the loss of the contribution of the red color component to the brightness. Upon completion, process 221 transfers to TRANSFORM ALL COLOR COMPONENTS OF IMAGE TO CHROMATIC COMPONENTS OF SECOND COLOR SPACE process 222.

For the example being considered, TRANSFORM ALL COLOR COMPONENTS OF IMAGE TO CHROMATIC COMPONENTS OF SECOND COLOR SPACE process 222 transforms first, second, and third color components, e.g., color components R, G, B in the RGB color space, to chromatic components Cb, Cr in the YCbCr color space. Note that luminance component Y is a grayscale component and so is not considered a color component in the YCbCr color space. Processes 221 and 222 together generate components Ynew, Cb, Cr for the received color image. Processes 221 and 222 may be executed either in sequential order, or in parallel; the FIG. 2 sequence is merely illustrative.

Stereoscopic displays or other video displays typically receive color component inputs in the RGB color space. Accordingly, after processes 221 and 222 are complete, processing transfers to TRANSFORM COLOR COMPONENTS IN SECOND COLOR SPACE TO NEW COLOR COMPONENTS IN FIRST COLOR SPACE 223.

TRANSFORM COLOR COMPONENTS IN SECOND COLOR SPACE TO NEW COLOR COMPONENTS IN FIRST COLOR SPACE 223 transforms components Ynew, Cb, Cr in second color space YCbCr to new color components Rnew, Gnew, Bnew in first color space RGB. New color components Rnew, Gnew, Bnew are contrast enhanced color components for the received color image. Upon completion, process 223 transfers to ALL PIXELS check operation 224.

All PIXELS check operation 224 determines whether all the pixels in the input color image have been processed. If all the pixels have been processed, check operation 224 transfers to TRANSMIT COLOR IMAGE process 230, and otherwise processes 221 to 223 are repeated.

Thus, in this aspect, processes 221 to 223 are performed for each pixel in the received color image. After all the pixels are processed, TRANSMIT ENHANCED COLOR IMAGE process 230 sends the color image with enhanced contrast to a destination device, e.g., to a display device.

Sequential processes 221, 222, and 223 are used only for ease of discussion and processes 221, 222, and 223 are not intended to be limited to this specific sequence. Those knowledgeable in the field understand that processes 221 to 223, for example, can be implemented as a single transformation, or can be performed in parallel for groups of pixels. For example, the transformation from the RGB color space to the YCbCr color space for a pixel is known. The transformation starts with a basic transform, which can be represented as:

$$\begin{pmatrix} Y \\ Cb \\ Cr \end{pmatrix} = T * \begin{pmatrix} R \\ G \\ B \end{pmatrix} \qquad (1)$$

where matrix T is $$T = \begin{pmatrix} t11 & t12 & t13 \\ t21 & t22 & t23 \\ t31 & t32 & t33 \end{pmatrix} \qquad (2)$$

Coefficients tij in matrix T are numbers that are known and defined in standards publications. Matrix T is a known standards transformation that maps all color components in the RGB color space to luminance and chromatic components in the YCbCr color space. (As noted above, the shift process is not considered here, as it cancels out over the complete method.) For example, the YCbCr color space is defined in the ITU-R BT.601-5 [1] and ITU-R BT.709-5 [2] standards of ITU (International Telecommunication Union). These standards give concrete definitions for coefficients of conversion between RGB and YCbCr color spaces for normalization and quantization of digital signals. Thus, matrix T is an example of a transformation that is referred to herein as a standards transformation and that transforms all color components of the first color space into all components of the second color space.

Thus, in this representation, $$Y = t11*R + t12*G + t13*B \qquad (3a)$$

$$Cb = t21*R + t22*G + t23*B \qquad (3b)$$

$$Cr = t31*R + t32*G + t33*B \qquad (3c)$$

Definition (3a) is an example of a standards transformation (ignoring any shift) that maps all color components of a first color space into a brightness component of a second color space. As just described, this transformation is defined by industry standards and the values of coefficients t11, t12, and t13 are defined by those industry standards. Therefore, definition (3a) is referred to as a standards transformation of color components in a first color space to a brightness component in a second color space.

Returning to process 221, intermediate brightness component Ygb is generated, in one aspect, using only color components G and B, e.g., $$Ygb = t12*G + t13*B \qquad (4a)$$

Definition (4a) is a first example of a transformation that maps color components in the first color space to an intermediate brightness component in a second color space. This transformation is not a standards transformation because the value of coefficient t11 is set to zero and the value of coefficient t11 in the standards transformation is not used. This transformation eliminates any contribution of red color component R to the intermediate brightness component.

As explained more completely below, process 221 further processes intermediate brightness component Ygb to generate a modified brightness component Ynew. Upon completion, process 221 transfers to process 222.

In process 222, chromatic components Cb, Cr are generated using all three color components R, B, and G, i.e., $$Cb = t21*R + t22*G + t23*B \quad (4b)$$

$$Cr = t31*R + t32*G + t33*B \quad (4c)$$

Expressions (4b) and (4c) are examples of transformations that map all color components in the first color space to chromatic components in the second color space.

Thus, processes 221 and 222 can be represented as $$\begin{pmatrix} Ynew \\ Cb \\ Cr \end{pmatrix} = T1 * \begin{pmatrix} R \\ G \\ B \end{pmatrix} \quad (5)$$

where $$T1 = \begin{pmatrix} 0 & t12' & t13' \\ t21 & t22 & t23 \\ t31 & t32 & t33 \end{pmatrix}$$

and where coefficients t12' and t13' are the coefficients obtained by processing the intermediate brightness component to compensate for the loss of the contribution of the red component.

Process 223 can be represented as:

$$\begin{pmatrix} Rnew \\ Gnew \\ Bnew \end{pmatrix} = T^{-1} * \begin{pmatrix} Ynew \\ Cb \\ Cr \end{pmatrix}$$

where matrix $T^{-1}$ is the inverse of standards matrix T. The transformations performed by processes 221 to 223 are:

$$\begin{pmatrix} Rnew \\ Gnew \\ Bnew \end{pmatrix} = T^{-1} * T1 * \begin{pmatrix} R \\ G \\ B \end{pmatrix} \quad (6)$$

which is $$\begin{pmatrix} Rnew \\ Gnew \\ Bnew \end{pmatrix} = A1 * \begin{pmatrix} R \\ G \\ B \end{pmatrix}$$

where A1 is $T^{-1}*T1$. Note that if the shifts in the two transformations had been included, when definition (6) is used, the shifts cancel out. Thus, in one aspect, processes 221 to 223 are implemented as a single transformation that maps the color components of the input color image to color components of an enhanced contrast color image.

In the above example, the input color image and the transmitted color image were assumed to be in the same color space. However, in some aspects, this may not be true. For example, the input color image, i.e., the color image received in process 210, could be in the YCbCr color space or in some other color space. In this case, each pixel in the received color image would be transformed from the YCbCr color space to the RGB color space and processes 221 to 223 performed as described above. While in this case three color space transformations are used, YCbCr color space to RGB color space, RGB color space to YCbCr color space, and YCbCr color space to RGB color space, the three transformation processes can be implemented as a single transformation.

For a general XYZ color space where XYZ represent the components of the input color image, the three color space transformations used are XYZ color space to RGB color space, RGB color space to YCbCr color space, and YCbCr color space to RGB color space. Again, the three transformation processes can be implemented as a single transformation. However, in the examples herein, the processes in the methods typically are presented as separate transformations to assist in the understanding of the methods. This is illustrative only and is not intended to limit the local contrast enhancement methods to the specific transformation sequences presented. One knowledgeable in the field can combine the sequence of transformations into a single transformation, or into other sequences that are advantageous for a particular application.

FIGS. 4 to 7 are process flow diagrams of different implementations of LOCAL CONTRAST ENHANCEMENT process 220 (FIG. 2). The difference in each of the implementations is the implementation of process 221. Processes 222 and 223 are the same in each of the implementations. Each of the implementations is described more completely below. Each of these implementations enhances the contrast of the input color image via an implementation of process 221, while keeping the true color of the input color image unchanged via process 222.

In the following implementations, the RGB color space and the YCbCr color space are used. Again, the use of these color spaces is illustrative only and is not intended to be limiting to these specific color spaces.

Figure 4A:
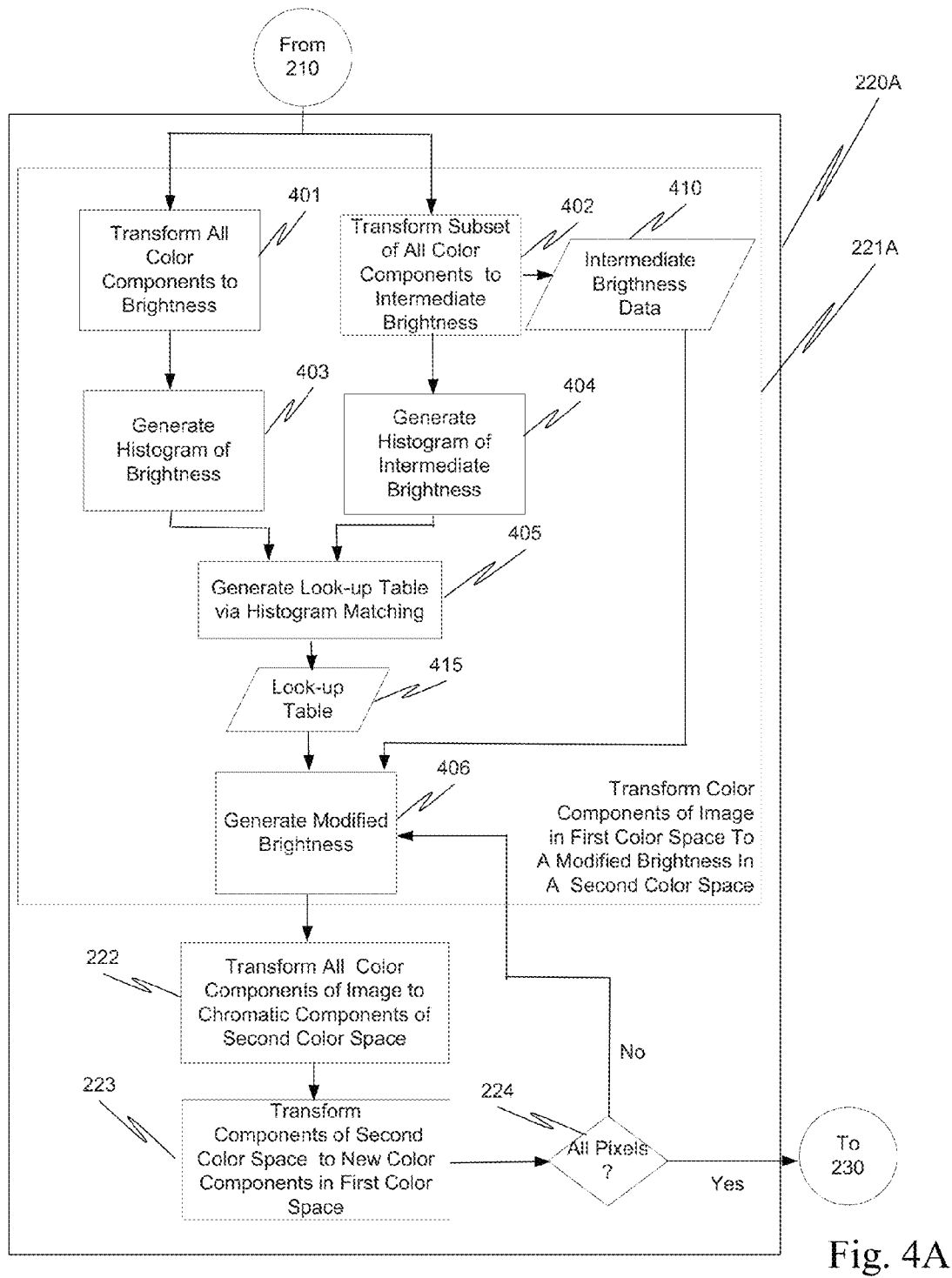
FIG. 4A is a process flow diagram of a local contrast enhancement process that utilizes histogram matching process.

In FIG. 4, TRANSFORM COLOR COMPONENTS OF IMAGE IN FIRST COLOR SPACE TO A MODIFIED BRIGHTNESS IN A SECOND COLOR SPACE process 221A uses a histogram matching process to generate a new brightness component for each pixel in the input color image. Specifically, TRANSFORM ALL COLOR COMPONENTS TO BRIGHTNESS process 401 generates for each pixel a brightness component in the second color space using each of the color components in the first color space. For the RGB color space and the YCbCr color space, in this example, display image controller 130 uses standards definition (3a) above to generate a luminance component Y for each pixel using the red, green, and blue color components R, G, B for that pixel in the input color image. Upon completion, TRANSFORM ALL COLOR COMPONENTS TO BRIGHTNESS process 401 transfers processing to GENERATE HISTOGRAM OF BRIGHTNESS process 403.

In GENERATE HISTOGRAM OF BRIGHTNESS process 403, a histogram is generated. In this example, luminance component Y is an eight-bit grayscale and can have any value from zero to 255. In the histogram, the possible grayscale values, i.e., brightness values, are plotted on an x-axis. A height of a bar for each of the possible luminance component values represents the number of pixels in the input color image having that brightness value.

Figure 4B:
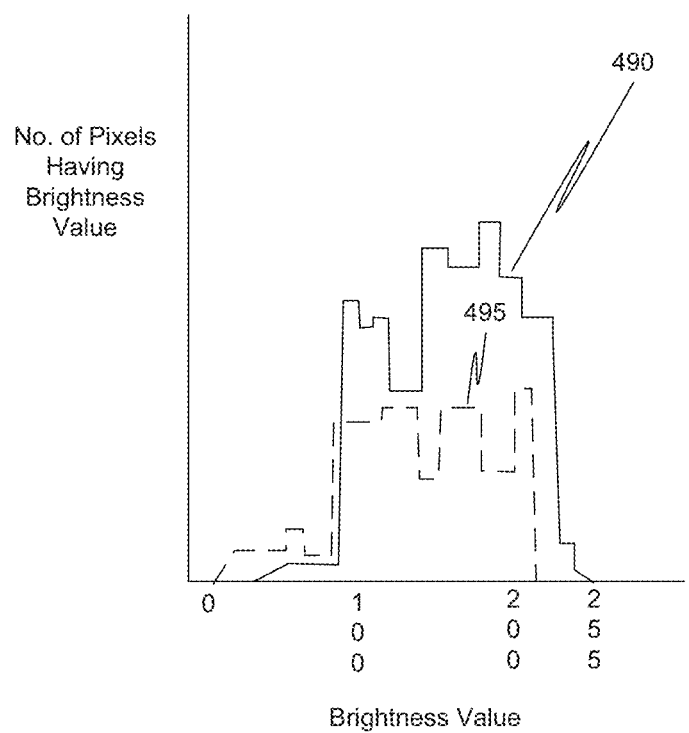
FIG. 4B is a representation of two histograms used in the histogram matching process of FIG. 4A.

Thus, if none of the pixels have the brightness value, the height of the bar for that brightness value is zero. If a hundred of the pixels have a brightness value the height of the bar for that brightness value is one hundred. If a curve is drawn connecting the center of the top of each bar, a curve 490 such as that shown in FIG. 4B is obtained. Curve 490 is not based upon any actual color image and is presented to assist in visualizing process 221A.

TRANSFORM SUBSET OF ALL COLOR COMPONENTS TO INTERMEDIATE BRIGHTNESS process 402 generates for each pixel an intermediate brightness component in the second color space using less than all of the color components in the first color space, e.g., a subset of all the color components. For the RGB color space and the YCbCr color space, in this example, display image controller 130 uses definition (4a) above to generate an intermediate brightness component Ygb for each pixel using the green and blue color components G, B for that pixel in the input color image. Intermediate brightness component Ygb for each pixel is stored in a memory, in one aspect, as INTERMEDIATE BRIGHTNESS DATA 410. This is illustrative only and is not intended to be limiting. For example, if sufficient memory is not available, intermediate brightness component Ygb can be generated as needed, e.g., generated on the fly.

In some aspects, process 402 can use the scaling or bias processes that are described more completely below. For example, the intermediate brightness component for each pixel could be multiplied by a scale factor, either a global scale factor or an adaptive scale factor. Upon completion, TRANSFORM SUBSET OF ALL COLOR COMPONENTS TO INTERMEDIATE BRIGHTNESS process 402 transfers processing to GENERATE HISTOGRAM OF INTERMEDIATE BRIGHTNESS process 404.

In GENERATE HISTOGRAM OF INTERMEDIATE BRIGHTNESS process 404, a second histogram is generated. In this example, intermediate luminance component Ygb is an eight-bit grayscale and so can have any value from zero to 255. When a curve is drawn connecting the center of the top of each bar, a curve 495 such as that shown in FIG. 4B is obtained. Curve 495 also is not based upon any actual color image and is presented to assist in visualizing process 221A.

Upon completion of both GENERATE HISTOGRAM OF BRIGHTNESS process 403 and GENERATE HISTOGRAM OF INTERMEDIATE BRIGHTNESS process 404, processing by display image controller 130 transfers to GENERATE LOOK-UP TABLE VIA HISTOGRAM MATCHING process 405. In process 405, intermediate luminance component Ygb for a pixel is mapped to luminance component Y for that pixel using histogram matching and the results is a brightness correction factor for each pixel that is stored in a memory in LOOK-UP TABLE 415. In the example, the contribution to luminance by the red color component has not been used in determining intermediate luminance component Ygb.

Thus, the global luminance based on the integration of intermediate luminance component Ygb over the color image is less than the global luminance based on the integration of luminance component Y, which includes the contribution to the luminance component from the red component, over the color image. Process 405, via histogram matching, generates a brightness correction factor for each pixel that adjusts the global luminance based on intermediate luminance component Ygb to match the global luminance based on luminance component Y so that the overall brightness of the color image is conserved. Stated in another way, the area under curve 495 is adjusted to approximate the area under curve 490 by the histogram matching process so brightness correction factors in the look-up table are obtained that map intermediate luminance component Ygb to a new modified luminance component Ynew, as described more completely below. Processes 401 to 405 are overhead that are performed to generate LOOK-UP TABLE 415.

Histogram matching is well know to those knowledgeable in the field and so is not discussed in detail. See for example, Anil K. Jain, "Histogram Modeling", *Fundamental of Digital Image Processing*, Section 7.3, Prentice Hall, pp 241-244 (1989), which is incorporated herein by reference in its entirety. Histogram matching to obtain a brightness correction factor for each pixel that maps the intermediate luminance component Ygb of a pixel to a new modified luminance component Ynew for that pixel is an example of an adaptive process to correct the brightness for loss of a color component.

In an adaptive process, an adaptive correction factor is obtained, based on a characteristic or characteristics of a set of pixels, for that set of pixels. The set of pixels contains less than all the pixels in the color image and may contain a single pixel. The characteristic or characteristics are representative of the pixels in the set. Thus, different sets of pixels may have different brightness correction factors, e.g., the brightness correction factor is adapted for the characteristic or characteristics of the set of pixels and can vary from set to set of pixels. When a brightness correction factor is generated for a set of pixels based on at least one characteristic of the set of pixels and when the set of pixels includes less than all the pixels in the color image, the brightness correction factor is referred to herein as an adaptive brightness correction factor.

Upon completion of process 405, the look-up table is available, and processes 406, 222, and 223 are performed for each pixel. For a current pixel, GENERATE MODIFIED BRIGHTNESS process 406 retrieves intermediate luminance component Ygb from INTERMEDIATE BRIGHTNESS DATA 410 and the corresponding brightness correction factor from LOOK-UP TABLE 415. The intermediate luminance component Ygb and the corresponding brightness correction factor are multiplied together to generate the modified brightness for that pixel. Process 406 then transfers to process 222.

Processes 222 and 223 are the same as described above, and so that description is incorporated herein by reference. When not all the pixels have been processed, ALL PIXELS check operation 224 transfers to GENERATE MODIFIED BRIGHTNESS process 406.

TRANSFORM COLOR COMPONENTS OF IMAGE IN FIRST COLOR SPACE TO A MODIFIED BRIGHTNESS IN A SECOND COLOR SPACE process 221A uses the histogram matching process to effectively preserve the brightness of the original color image while enhancing the contrast. Thus, regions of process 221A do not experience saturation, e.g., images of surgical instruments do not saturate.

The histogram mapping is used, in one aspect, in applications with minimal instances of fast motion images and/or illumination changes. Also, some quantization artifacts have been observed due to the global luminance mapping. Finally, the number of operations required to generate the histograms and to perform the histogram matching requires that display image controller 130 have adequate memory and processing power to perform the operations within the time frame associated with each color image in minimally invasive teleoperated surgical system 100.

Figure 5:
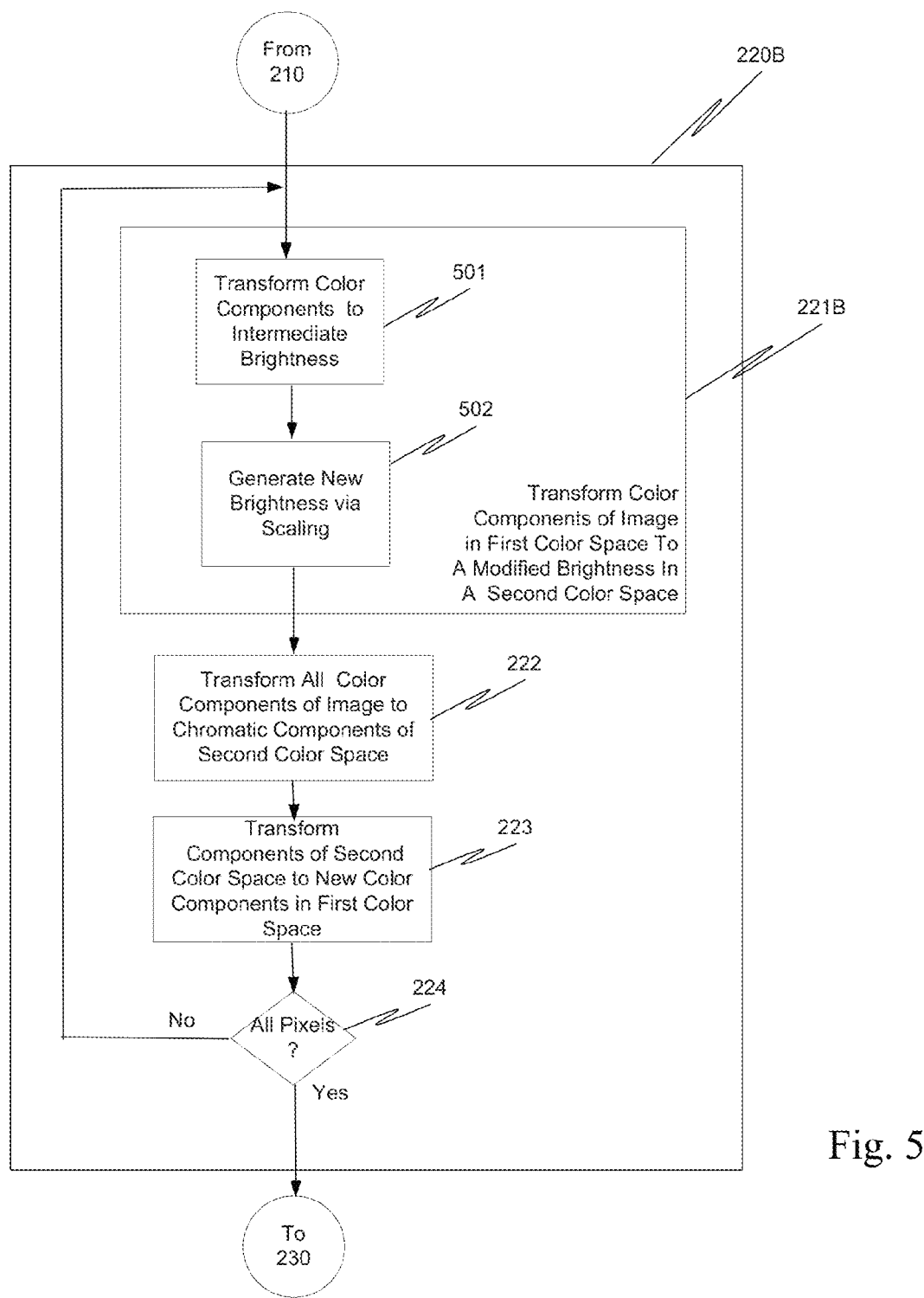
FIG. 5 is a process flow diagram of a local contrast enhancement process that utilizes a scaling process.

Referring to FIG. 5 and LOCAL CONTRAST ENHANCEMENT process 220B, TRANSFORM COLOR COMPONENTS TO INTERMEDIATE BRIGHTNESS process 501 of TRANSFORM COLOR COMPONENTS OF IMAGE IN FIRST COLOR SPACE TO A MODIFIED BRIGHTNESS OF SECOND COLOR SPACE process 221B generates a modified brightness component in the second color space using less than all the color components of the first color space. As an example, again the first color space in process 221B is the RGB color space, and the second color space is the YCbCr color space. In this example, display image controller 130 (FIG. 1) uses definition (4a) above to generate an intermediate brightness component Ygb for each pixel using the green and blue color components G, B for that pixel in the input color image, i.e., $$Ygb=t12*G+t13*B$$

Process 501 than transfers to GENERATE NEW BRIGHTNESS VIA SCALING process 502. In one aspect, process 502 generates a new modified brightness component by multiplying the intermediate brightness component by a constant scale factor. For example, for a scale factor s $$Ynew=s*Ygb=s*t12*G+s*t13*B \qquad (7)$$

where luminance component Ynew is the new modified brightness component. In one aspect, scale factor s was selected as 1.3, as explained more completely below. Upon completion, process 502 transfers to TRANSFORM ALL COLOR COMPONENTS OF IMAGE TO CHROMATIC COMPONENTS OF SECOND COLOR SPACE process 222.

For the example being considered, TRANSFORM ALL COLOR COMPONENTS OF IMAGE TO CHROMATIC COMPONENTS OF SECOND COLOR SPACE process 222 transforms first, second, and third color components, e.g., color components R, G, B in the RGB color space to chromatic components Cb, Cr in the YCbCr color space. Note that luminance component Ynew is a grayscale component and so is not considered a color component in the YCbCr color space. Processes 221B and 222 together generate components Ynew, Cb, Cr for the received color image.

Upon completion process 222 transfers processing to TRANSFORM COLOR COMPONENTS IN SECOND COLOR SPACE TO NEW COLOR COMPONENTS IN FIRST COLOR SPACE 223, which in turn transforms components Ynew, Cb, Cr in second color space YCbCr to new color components Rnew, Gnew, Bnew in first color space RGB. New color components Rnew, Gnew, Bnew are contrast enhanced color components for the received color image. In one aspect, processes 221B to 224 are performed for each pixel in the received color image as described above.

Thus, processes 221B and 222 can be represented as $$\begin{pmatrix} Ynew \\ Cb \\ Cr \end{pmatrix} = T2 * \begin{pmatrix} R \\ G \\ B \end{pmatrix}$$

where $$T2 = \begin{pmatrix} 0 & s*t12 & s*t13 \\ t21 & t22 & t23 \\ t31 & t32 & t33 \end{pmatrix}$$

Note that in this example, coefficient t12' above (See definition (5)) is S*t12, and coefficient t13' above is s*t13.

Process 223 can be represented as:

$$\begin{pmatrix} Rnew \\ Gnew \\ Bnew \end{pmatrix} = T^{-1} * \begin{pmatrix} Ynew \\ Cb \\ Cr \end{pmatrix}$$

where matrix $T^{-1}$ is the inverse of matrix T and $$\begin{pmatrix} Rnew \\ Gnew \\ Bnew \end{pmatrix} = T^{-1} * T2 * \begin{pmatrix} R \\ G \\ B \end{pmatrix} \qquad (8)$$

which is $$\begin{pmatrix} Rnew \\ Gnew \\ Bnew \end{pmatrix} = A2 * \begin{pmatrix} R \\ G \\ B \end{pmatrix}$$

where A2 is $T^{-1}*T2$. Thus, in one aspect, processes 221B to 223 are implemented as a single transformation that converts the color components of the input color image to color components of an enhanced contrast color image.

In the above aspect that used a scale factor s, one color component in the first color space is not used in determining a modified brightness component in the second color space. Specifically, an intermediate brightness component is generated that does not include a contribution from the unused color component—the red color component in the above examples. To compensate for the loss of the contribution of the unused color component to the brightness, the intermediate brightness component is scaled to generate a new modified brightness component. The scale factor is chosen to achieve a best overall brightness in the contrast enhanced color image.

In one aspect, to obtain an initial estimate for the scale factor, a global average pixel value for the red color component of the pixels in a color image was determined, and global average pixel values for each of the blue and green color components were determined. The global average value for the red color component for all the pixels in the color image was 200 and the global average values for the blue and green color components were 128. Dividing these two values indicated that a scale factor of about 1.5 was a reasonable initial value to use in empirically determining a scale factor.

Thus, in one aspect, the transformation defined by definition (8) above was implemented in display image controller 130. Values of 1.3, 1.4, and 1.5 for scale factor s were used. While all the scale factors provided satisfactory contrast enhancement, the color images produced using a scale factor of 1.3 were preferred by a majority of the individuals that viewed the color images generated using the different scale factors.

The perception of the enhancement in contrast was best for a scale factor of 1.5. However, the amount of light reflected from tissue is different from the amount of light reflected from instruments in the field of view of stereoscopic endoscope 112 and so saturation becomes an issue. Scale factor of 1.3 was selected as giving the overall best result when both contrast enhancement and saturation were considered. The processing power required to implement the transformation represented by definition (8) is the least of the various implementations considered. This permits consideration of implementation of the transformation in other than display image controller 130. For example, a hardware circuit that performed the transformation of definition (8) could be implemented in image capture system 120 in some aspects.

The use of the same global scaling factor s for all the pixels of the color image in generating the new modified brightness component in TRANSFORM SUBSET OF COLOR COMPONENTS OF IMAGE IN FIRST COLOR SPACE TO A MODIFIED BRIGHTNESS OF SECOND COLOR SPACE process 221B is illustrative only and is not intended to be limiting. In one aspect, the scale factor in TRANSFORM SUBSET OF COLOR COMPONENTS OF IMAGE IN FIRST COLOR SPACE TO A BRIGHTNESS OF SECOND COLOR SPACE process 221B is adaptively modified for different regions of the color image and so the scale factor is not a global scale factor, but rather is referred to as an adaptive scale factor. The adaptive scale factor is an example of the adaptive brightness correction factor, as defined above.

For example, a 16 pixel by 16 pixel block could be used to determine average pixel values for at least two color components in the block—the color component not being using in generating the modified luminance component and at least one of the other color components. The ratio of the average pixel value of the red color component to the average pixel value of the green color component could be used as the scale factor for that block. Thus, the scale factor is determined based on characteristics of the pixels in the block. The scale factor is an adaptive scale factor because a scale factor is generated for each block of pixels in the color image based on at least one characteristic of the pixels in the block. Each block of pixels is a set of pixels that includes less than all the pixels in the color image.

Thus, a block of pixels associated with a surgical instrument would have a scale factor different from a block of pixels associated with tissue that included many block vessels. Thus, the scaling factor is adapted based on the characteristics of the pixels in a block. Also, depending on the processing power available, the block size may also adaptively adjusted, e.g., the number of pixels included in a block may be adjusted by sampling for changes indicative of the surgical instrument for example or for changes indicative of other features in the color image known to have different reflective properties.

Figure 6:
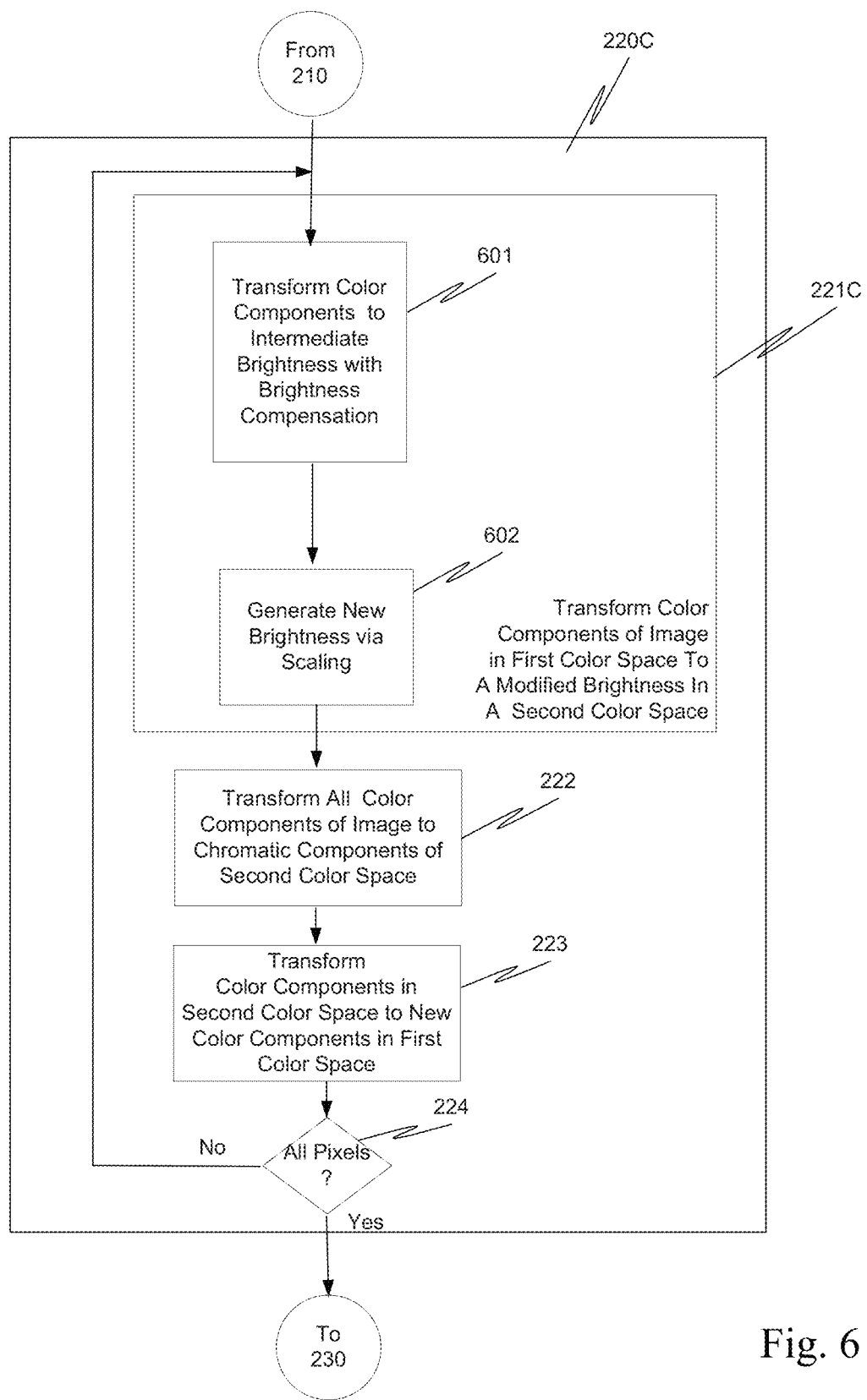
FIG. 6 is a process flow diagram of a local contrast enhancement process that utilizes brightness compensation process and a scaling process.

Referring to FIG. 6, a process flow diagram for yet another implementation of LOCAL CONTRAST ENHANCEMENT process 220C is presented. In the implementations described above of the LOCAL CONTRAST ENHANCEMENT process, one color component in the first color space is not used in generating a new modified brightness component in the second color space.

For pixels that include only the color component not used in generating the new modified brightness component, or for pixels that include primarily the color component not used, the new modified brightness component for such pixels is black or near black. Consider for example a pixel in the RGB color space that has only a red color component, e.g. both the green and blue color components are zero for the pixel. When the modified new brightness is generated for the pixel based on definition (7), the modified new brightness has a value zero, which is black. The effect of this for surgical images is that the arteries or blood might appear darker than is anticipated by the surgeon because the red color component was not used in generating the new modified brightness component for the arteries in the color image.

To make the arteries or blood appear more normal, process 220C (FIG. 6) uses both scaling and brightness compensation. In one aspect, a constant C is added to definition of the intermediate brightness component, e.g., $$Ygb\_comp = t12*G + t13*B + C \quad (9a)$$

as the brightness compensation.

In another aspect, the red component R is maintained in the definition of the intermediate brightness component, but the contribution of red component R to the intermediate brightness component is biased by a bias factor Rbias, where bias factor Rbias is less than one and equal to or greater than zero. In this aspect, intermediate brightness component Ygb is defined as $$Ygb\_comp = Rbias*(t11*R) + t12*G + t13*B \quad (9b)$$

Notice that definition (4a) above is a special case of definition (9b) with bias factor Rbias equal to zero. Also, in some aspect, definitions (9a) and (9b) can be used in combination. For example, the combination of the two definitions might help to generate a brighter color image with contrast enhancement even in dark corners of the surgical image.

In the following examples, bias factor Rbias is used. However, this is illustrative only and is not intended to be limiting to this specific form of brightness compensation. In view of this disclosure, those knowledgeable in the field can select a brightness compensation that gives the desired result for the local contrast enhancement.

Thus, in this aspect, TRANSFORM COLOR COMPONENTS TO INTERMEDIATE BRIGHTNESS WITH BRIGHTNESS COMPENSATION process 601 of TRANSFORM COLOR COMPONENTS OF IMAGE IN FIRST COLOR SPACE TO A MODIFIED BRIGHTNESS OF SECOND COLOR SPACE process 221C generates a modified brightness component in the second color space using all the color components of the first color space. Process 221C biases the contribution of one color component. As an example, again the first color space in process 221C is the RGB color space, and the second color space is the YCbCr color spaces. In this example, display image controller 130 (FIG. 1) uses definition (9b) above to generate an intermediate brightness component Ygb_comp for each pixel using the red, green, and blue color components R, G, B for that pixel in the input color image. Various values of bias factor Rbias have been used, e.g., 0.15 and 0.23. In one aspect, bias factor Rbias is empirically determined by using a range of values and then selecting the one that is perceived as providing the most local contrast enhancement in comparison to the original color image while preserving overall image quality.

Process 601 transfers to GENERATE NEW BRIGHTNESS VIA SCALING process 602. In one aspect, process 602 generates a new brightness by multiplying the intermediate brightness component by a constant scale factor. For example, for a scale factor s $$Ynew = s*Ygb\_comp$$
$$= s*Rbias*(t11*R) + s*t12*G + s*t13*B$$

where luminance component Ynew is the new modified brightness component. Upon completion, process 502 transfers to TRANSFORM ALL COLOR COMPONENTS OF IMAGE TO CHROMATIC COMPONENTS OF SECOND COLOR SPACE process 222.

For the example being considered, TRANSFORM ALL COLOR COMPONENTS OF IMAGE TO CHROMATIC COMPONENTS OF SECOND COLOR SPACE process 222 transforms first, second, and third color components, e.g., color components R, G, B in the RGB color space to color components Cb, Cr in the YCbCr color space. Processes 221C and 222 together generate components Ynew, Cb, Cr for the received color image.

Upon completion process 222 transfers processing to TRANSFORM COLOR COMPONENTS IN SECOND COLOR SPACE TO NEW COLOR COMPONENTS IN FIRST COLOR SPACE 223, which in turn transforms components Ynew, Cb, Cr in second color space YCbCr to new color components Rnew, Gnew, Bnew in first color space RGB. New color components Rnew, Gnew, Bnew are contrast enhanced color components for the received color image. In one aspect, processes 221C to 224 are performed for each pixel in the received color image.

Thus, processes 221C and 222 can be represented as $$\begin{pmatrix} Ynew \\ Cb \\ Cr \end{pmatrix} = T3 * \begin{pmatrix} R \\ G \\ B \end{pmatrix}$$

where $$T3 = \begin{pmatrix} s*Rbias*t11 & s*t12 & s*t13 \\ t21 & t22 & t23 \\ t31 & t32 & t33 \end{pmatrix}$$

Process 223 can be represented as:

$$\begin{pmatrix} Rnew \\ Gnew \\ Bnew \end{pmatrix} = T^{-1} * \begin{pmatrix} Ynew \\ Cb \\ Cr \end{pmatrix}$$

where matrix $T^{-1}$ is the inverse of matrix T and $$\begin{pmatrix} Rnew \\ Gnew \\ Bnew \end{pmatrix} = T^{-1} * T3 * \begin{pmatrix} R \\ G \\ B \end{pmatrix}$$

which is $$\begin{pmatrix} Rnew \\ Gnew \\ Bnew \end{pmatrix} = A3 * \begin{pmatrix} R \\ G \\ B \end{pmatrix}$$

where A3 is $T^{-1}*T3$. Thus, in one aspect, processes 221C to 223 are implemented as a single transformation that converts the color components of the input color image to color components of an enhanced contrast color image.

Again, note that if the input color image is in the YUV color space instead of the RGB color space, the transformation for the YUV color space to the RGB color space is known and defined by an industry standard. Thus, transformation of the color image in the YUV color space to the RGB color space could be combined with transformation A3 to generate a single transformation that takes pixels in the YUV color space and transforms them to pixels having color components Rnew, Gnew, Bnew in the RGB color space.

The enhanced contrast color images generated with the bias and scaling mapping process have better perceived contrast because red structures in the color images appear more natural than those same structures when only scaling is used. However, in some regions of the color image, saturation was observed. The color images did not appear to be effected by illumination changes or fast motion. The processing requirements for this method are low.

The use of the same scaling factor for all the pixels and the use of the same bias factor for the red component of all pixels in generating the new brightness in TRANSFORM COLOR COMPONENTS OF IMAGE IN FIRST COLOR SPACE TO A MODIFIED BRIGHTNESS OF SECOND COLOR SPACE process 221C is illustrative only and is not intended to be limiting. Again, adaptive procedures can be used to select the scale factor and/or the bias factor based on characteristics of a portion of the color image. For example, the bias factor is used only in blocks where the average red component value is a certain percentage greater than the average green color component value. The techniques described above for adaptively determining the scale factor are applicable to this method and are incorporated herein by reference.

Figure 7:
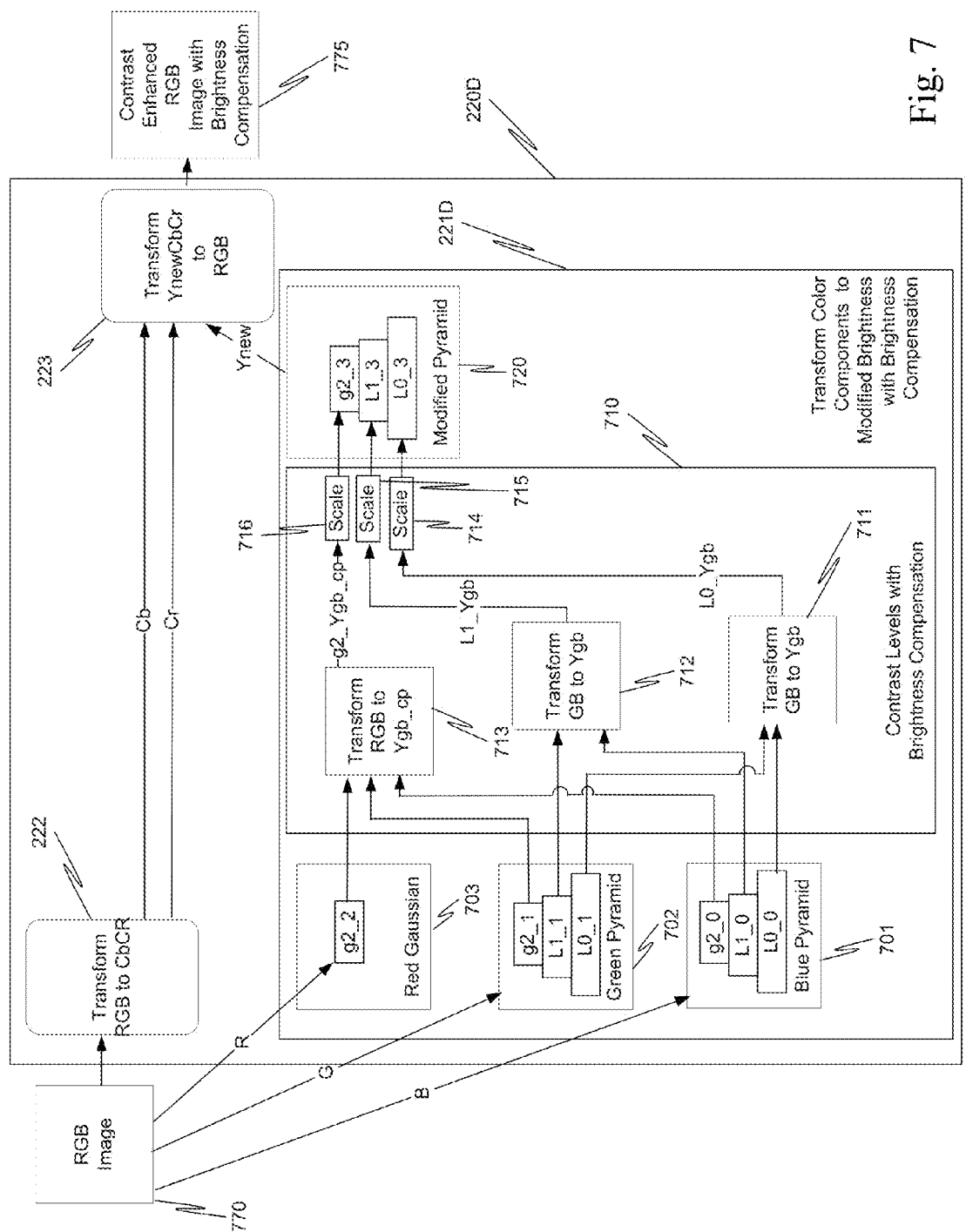
FIG. 7 process flow diagram of a local contrast enhancement process that utilizes a Laplacian pyramid process.

Referring to FIG. 7, a process flow diagram for yet another implementation of LOCAL CONTRAST ENHANCEMENT process 220D is presented. Again, to make the color of arteries or blood appear more normal, process 220D (FIG. 7) uses both scaling and brightness compensation. To compensate for the saturation mentioned above, a multi-resolution approach is employed to use different scaling factors and brightness compensations.

Briefly, a subset of components, e.g., green color component G and blue color component B, for pixels in input color image 770 is transformed into a plurality of multi-resolution Laplacian pyramids 701, 702. (See U.S. patent application Ser. No. 12/946,634 (filed 15 Nov. 2010, disclosing "SYSTEM AND METHOD FOR MULTI-RESOLUTION SHARPNESS TRANSPORT ACROSS COLOR CHANNELS"), which is incorporated herein by reference, for additional information on using Laplacian pyramids.)

Color components, which were not included in the subset of components, for pixels in input color image 770 are transformed into a Gaussian image representation 703. The plurality of multi-resolution Laplacian pyramids 701, 702 and the Gaussian image representation 703 provide inputs to a CONTRAST LEVELS WITH BRIGHTNESS COMPENSATION process 710. Process 710 generates a new multi-resolution Laplacian pyramid 720. New multi-resolution Laplacian pyramid 720 is used to generate a new modified luminance component Ynew for each pixel in the color image.

To be more specific, in this example, input color image includes a plurality of color components R, B, G for each pixel in the color image. Green and blue color components G, B for the pixels are each transformed to a multi-resolution Laplacian representation via smoothing, subtraction, and subsampling (details can be found in the following reference: P. Burt and T. Adelson, "The Laplacian pyramid as a Compact Image Code", IEEE Trans. Communications, 9:4, 532-540, 1983, which is incorporated herein by reference).

Here, a multi-resolution representation includes a plurality of transformation level representations. For a three level Laplacian pyramid, there are two Laplacian levels L0, L1, which are a sequence of error images. Each Laplacian level is the difference between two levels of a Gaussian pyramid as described by Burt et al. Since there are only three levels in this example, there is no fourth level to serve as a prediction for level L2 and so level L2 is set equal to the Gaussian pyramid level g2. If Laplacian level L0 is 1920 by 1080 pixels, Laplacian level L1 is 960 by 540 pixels, and so on.

Herein an underscore and a number after the level number are used to distinguish between different data at a particular level in a pyramid and between pyramids. The number of levels used in the Laplacian pyramid is illustrative only and is not intended to be limiting to the number of levels used in this example.

As illustrated in FIG. 7, in this example, Laplacian pyramid 701 and Laplacian pyramid 702 are constructed for blue color component B and green color component G in input color image 770. As just noted, in this example, there are three levels of each pyramid, L0, L1, g2. In each pyramid, top level g2 is the lowest resolution level and the bottom level L0 is the highest resolution level. The red color component for the pixels in input color image 770 is converted to a Gaussian level g2_2.

Process 710 uses information in the different levels of Laplacian pyramids 701 and 702 and Gaussian level 703 to generate corresponding information in modified pyramid 720. Specifically, a first TRANSFORM SUBSET OF COLOR COMPONENTS TO INTERMEDIATE BRIGHTNESS process, which is indicated for this example in FIG. 7 as a first TRANSFORM GB to Ygb process 711, uses Laplacian level L0__0 of blue pyramid 701 and Laplacian level L0__1 of green pyramid 702 to generate a Level L0 intermediate luminance component L0_Ygb.

Similarly, a second TRANSFORM SUBSET OF COLOR COMPONENTS TO INTERMEDIATE BRIGHTNESS process, which is indicated for this example in FIG. 7 as a second TRANSFORM GB to Ygb process 712, uses Laplacian level L1__0 of blue pyramid 701 and Laplacian level L1__1 of green pyramid 702 to generate a Level L1 intermediate luminance component L1_Ygb. Both process 711 and process 712 used definition (4a) above in doing the transformations.

In process 710, a first TRANSFORM COLOR COMPONENTS TO INTERMEDIATE BRIGHTNESS WITH BRIGHTNESS COMPENSATION process, which is indicated for this example in FIG. 7 as TRANSFORM RGB to Ygb_cp process 713, uses Gaussian level g2__0 of blue pyramid 701, Gaussian level g2__1 of green pyramid 702, and Gaussian level g2__2 to generate a Level g2 intermediate luminance component with compensation g2_Ygb_cp. Process 713 used definition (9b) above in doing the transformation.

Next in process 710, each of the intermediate luminance components is scaled. Level L0 intermediate luminance component L0_Ygb is scaled in SCALE process 714 using a first scale factor. Level L1 intermediate luminance component L1_Ygb is scaled in SCALE process 715 using a second scale factor. Level g2 intermediate luminance component with compensation g2_Ygb_cp is scaled in SCALE process 716 using a third scale factor.

The first, second, and third scale factors used in SCALE processes 714, 715, 716, respectively may be the same scale factor, or may be different scale factors. In one aspect, the scale factors were different. The first scale factor was 1.5 for the highest resolution Laplacian level L0. The second scale factor was 1.4 for the intermediate resolution Laplacian level L1. The third scale factor was 1.3 for the lowest resolution Gaussian level g2.

The scaled outputs from processes 714, 715, 716 are Laplacian level L0__3, Laplacian level L1__3, and Gaussian level g2__3 of modified pyramid 720. The information in modified pyramid 720 is used to reconstruct, using the reconstruction process described by Burt et al. (which was incorporated by reference above), a new luminance component Ynew that includes a new modified luminance value for each pixel in the color image. The reconstruction process is known to those knowledgeable in the field and so is not considered in further detail herein.

Processes 222 and 223 are the same as those described above, and so that description is incorporated herein by reference to avoid repetition. Thus, process 220D converts an input color image 770 to an output color image 775 with enhanced contrast and brightness compensation.

The enhanced contrast color images generated with the pyramid mapping process have better perceived contrast because red structures in the color images appear more natural than those same structures when only scaling is used. Also, no saturation issues were observed, and the color images did not appear to be effected by illumination changes or fast motion. The number of operations required to generate the pyramids and perform the mapping process requires that display image controller 130 have adequate memory and processing power to perform the operations within the time frame associated with each color image in minimally invasive teleoperated surgical system 100.

As used herein, "first", "second", and "third" are adjectives used to distinguish between visible color components. Thus, "first", "second", and "third" are not intended to imply any ordering of the visible color components within the visible wavelength spectrum.

In the above description, the camera was mounted proximal to the endoscope. However, this is illustrative only and is not intended to be limiting. The process works the same irrespective of the relative locations of the viewing optics and the camera if the camera can acquire usable images from the light from the optics. For example, the processes and structures described herein can be utilized with a chip-on-stick endoscope. A chip-on-stick endoscope has a short optics segment with a camera located just behind the optics near the tip of the endoscope.

Also, a stereoscopic endoscope was used as an example. This also is illustrative only and is not intended to be limiting. A monoscopic endoscope could be used in place of the stereoscopic endoscope in the above examples. With the monoscopic endoscope only one of the left and right images would be acquired and processed as described above.

The above description and the accompanying drawings that illustrate aspects and embodiments of the present inventions should not be taken as limiting—the claims define the protected inventions. Various mechanical, compositional, structural, electrical, and operational changes may be made without departing from the spirit and scope of this description and the claims. In some instances, well-known circuits, structures, and techniques have not been shown or described in detail to avoid obscuring the invention.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of the device in use or operation in addition to the position and orientation shown in the figures. For example, if the device in the figures is turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations) and the spatially relative descriptors used herein interpreted accordingly. Likewise, descriptions of movement along and around various axes include various special device positions and orientations.

The singular forms "a", "an", and "the" are intended to include the plural forms as well, unless the context indicates otherwise. The terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

Memory refers to a volatile memory, a non-volatile memory, or any combination of the two. A processor is coupled to a memory containing instructions executed by the processor. This could be accomplished within a computer system, or alternatively via a connection to another computer via modems and analog lines, or digital interfaces and a digital carrier line.

Herein, a computer program product comprises a non-transitory medium configured to store computer readable code needed for any one or any combination of the operations described with respect to the local contrast enhancement module or in which computer readable code for any one or any combination of operations described with respect to the local contrast enhancement module is stored. Some examples of computer program products are CD-ROM discs, DVD discs, flash memory, ROM cards, floppy discs, magnetic tapes, computer hard drives, servers on a network and signals transmitted over a network representing computer readable program code. A non-transitory tangible computer program product comprises a non-transitory tangible medium configured to store computer readable instructions for any one of, or any combination of operations described with respect to the local contrast enhancement module or in which computer readable instructions for any one of, or any combination of operations described with respect to the local contrast enhancement module are stored. Non-transitory tangible computer program products include CD-ROM discs, DVD discs, flash memory, ROM cards, floppy discs, magnetic tapes, computer hard drives and other non-transitory physical storage mediums.

In view of this disclosure, instructions used in any one of, or any combination of operations described with respect to the augmented display system can be implemented in a wide variety of computer system configurations using an operating system and computer programming language of interest to the user.

All examples and illustrative references are non-limiting and should not be used to limit the claims to specific implementations and embodiments described herein and their equivalents. The headings are solely for formatting and should not be used to limit the subject matter in any way, because text under one heading may cross reference or apply to text under one or more headings. Finally, in view of this disclosure, particular features described in relation to one aspect or embodiment may be applied to other disclosed aspects or embodiments of the invention, even though not specifically shown in the drawings or described in the text.

We claim:

1. A method comprising:
transforming, by a processor, color components in a first color space into color components of a second color space, the color components in the first color space being color components of a first visual color image, the transforming the color components in the first color space into the color components of the second color space comprising:
transforming, by the processor, a first plurality of the color components of the first color space into a modified brightness component using a first transformation, wherein the modified brightness component represents a brightness component of the second color space, wherein the second color space includes a plurality of chromatic components in addition to the brightness component, and wherein the first transformation is different from a second standards transformation that transforms all color components of the first color space into a brightness component of the second color space; and
transforming, by the processor, all the color components of the first color space into the chromatic components of the second color space; and
transforming, by the processor, the modified brightness component and the chromatic components of the second color space into a plurality of new color components of a second visual color image, the plurality of new color components being in the first color space, wherein the plurality of new color components includes all the color components in the first color space, and wherein the second visual color image has enhanced contrast in comparison to the first visual color image;
transmitting, by the processor, the plurality of new color components to a device.

2. The method of claim 1 wherein all of the transforming processes are performed in a single transforming process.

3. The method of claim 1, further comprising:
transforming, by the processor prior to the transforming the first plurality of components, color components of the first visual color image in a third color space into the color components in the first color space, wherein the third color space is different from the first color space.

4. The method of claim 1, further comprising:
receiving the first visual color image from an endoscopic camera so that the first visual color image includes an image of a surgical site.

5. The method of claim 4, further comprising:
capturing light from a stereoscopic endoscope by the endoscopic camera, wherein the captured light comprises the first visual color image.

6. The method of claim 1,
wherein the first color space has red, green, and blue color components, and
wherein the second color space has a luminance component and two chromatic components.

7. The method of claim 6,
wherein the first plurality of color components is the blue color component and the green color component, and
wherein the modified brightness component in the second color space is a modified luminance component.

8. The method of claim 6,
wherein the first plurality of color components includes all colors components in the first color space except one color component.

9. The method of claim 1, wherein the transforming the first plurality comprises:
performing a scaling process.

10. The method of claim 9, wherein the scaling process is performed on less than all the color components in the first color space so that first plurality of color components includes less than all the color components in the first color space.

11. The method of claim 10, wherein the first plurality of color components includes a green color component.

12. The method of claim 9, wherein the performing the scaling process includes using a same scaling factor for the first plurality of color component for all pixels in the first visual color image.

13. The method of claim 9, wherein the performing the scaling process includes using an adaptive scaling factor.

14. The method of claim 1, wherein the transforming the first plurality includes performing a brightness compensation process so that the modified brightness component includes brightness compensation.

15. The method of claim 14, wherein the performing the brightness compensation process comprises:
biasing a coefficient in the second standards transformation for one of the color components in the first plurality prior to the transforming the first plurality, wherein the first plurality includes all the color components in the first color space; and further wherein the transforming the first plurality comprises:

transforming all the color components in the first color space to an intermediate brightness component in the second color space using a transformation including the biased coefficient.

16. The method of claim 15, wherein the transforming the first plurality further comprises:

scaling the intermediate brightness component to generate the modified brightness component with compensation.

17. The method of claim 14, wherein the transforming the first plurality comprises:

transforming less than all the color components in the first color space into a first intermediate brightness component in the second color space; and further wherein the performing the brightness compensation process comprises:

adding a constant to the first intermediate brightness component to obtain a second intermediate brightness component.

18. The method of claim 17, wherein the transforming the first plurality further comprises:

scaling the second intermediate brightness component to generate the modified brightness component with brightness compensation.

19. The method of claim 1, wherein the transforming the first plurality comprises generating a plurality of pyramids having a plurality of levels, wherein each level has a different image resolution.

20. The method of claim 1, wherein the transforming the first plurality comprises performing a histogram matching process, wherein the histogram matching process maintains the global brightness of the first visual color image in the second visual color image.

21. An apparatus comprising:

a camera, wherein the camera captures light and thereby creates a first visual color image having a first plurality of color components in a first color space;

a control system, coupled to the camera, including:

a contrast improvement module, wherein the contrast improvement module transforms the first visual color image to a second visual color image with enhanced contrast relative to the first visual color image by mapping the first plurality of color components into a modified brightness component and chromatic components of a second color space, and then mapping the modified brightness component and chromatic components to a new plurality of color components, in the first color space, of a second visual color image; and a display device coupled to the contrast improvement module to receive the second visual color image, wherein the display device displays the second visual color image with enhanced contrast relative to the first visual color image.

* * * * *